US010047392B2

(12) United States Patent
Ivankin et al.

(10) Patent No.: US 10,047,392 B2
(45) Date of Patent: Aug. 14, 2018

(54) FLUORESCENCE-BASED ANALYSIS OF BIOPOLYMERS USING NANOPORES

(71) Applicant: Northeastern University, Boston, MA (US)

(72) Inventors: Andrey Ivankin, Chicago, IL (US); Joseph Larkin, Dorchester, MA (US); Robert Henley, Boston, MA (US); Meni Wanunu, Boston, MA (US)

(73) Assignee: Northeastern University, Boston, MA (US)

( * ) Notice: Subject to any disclaimer, the term of this patent is extended or adjusted under 35 U.S.C. 154(b) by 82 days.

(21) Appl. No.: 15/119,859

(22) PCT Filed: Feb. 23, 2015

(86) PCT No.: PCT/US2015/017146
§ 371 (c)(1),
(2) Date: Aug. 18, 2016

(87) PCT Pub. No.: WO2015/127387
PCT Pub. Date: Aug. 27, 2015

(65) Prior Publication Data
US 2017/0058336 A1    Mar. 2, 2017

Related U.S. Application Data

(60) Provisional application No. 61/942,772, filed on Feb. 21, 2014.

(51) Int. Cl.
*C12Q 1/6869* (2018.01)
*G01N 21/64* (2006.01)
(Continued)

(52) U.S. Cl.
CPC ....... *C12Q 1/6869* (2013.01); *G01N 21/6408* (2013.01); *G01N 21/6428* (2013.01);
(Continued)

(58) Field of Classification Search
CPC ..... C12Q 1/6869; C12Q 1/68; G01N 21/6408
See application file for complete search history.

(56) References Cited

U.S. PATENT DOCUMENTS 6,015,714 A    1/2000 Baldarelli et al.
7,238,485 B2   7/2007 Akeson et al.
(Continued)

FOREIGN PATENT DOCUMENTS

WO    2011/106459 A2    9/2011
WO    2012088339        6/2012
(Continued)

OTHER PUBLICATIONS

Ivankin et al, Label-Free Optical Detection of Biomolecular Translocation through Nanopore Arrays, 2014, ACSNANO, 8, 10774-10781. (Year: 2014).*
(Continued)

*Primary Examiner* — Narayan Bhat
(74) *Attorney, Agent, or Firm* — Posternak Blankstein & Lund LLP

(57) ABSTRACT

Described herein are systems for analysis of biopolymers and complexes containing biopolymers based on optical measurement of ion flux through pores. Also described are methods of using such devices for analysis of biopolymers and complexes containing biopolymers, including methods of determining the nucleotide sequences of polynucleotides.

14 Claims, 11 Drawing Sheets

(51) Int. Cl.
G01N 33/487 (2006.01)
G01N 21/77 (2006.01)

(52) U.S. Cl.
CPC ... *G01N 21/6458* (2013.01); *G01N 33/48721* (2013.01); *G01N 2021/6439* (2013.01); *G01N 2021/7786* (2013.01)

(56) References Cited

U.S. PATENT DOCUMENTS

| 8,652,779 | B2 | 2/2014 | Turner et al. | |
|---|---|---|---|---|
| 2003/0098248 | A1* | 5/2003 | Vogel | B01L 3/5085 |
| | | | | 205/777.5 |
| 2007/0099191 | A1 | 5/2007 | Nair et al. | |
| 2007/0190542 | A1 | 8/2007 | Ling et al. | |
| 2011/0053284 | A1 | 3/2011 | Meller et al. | |
| 2012/0088235 | A1 | 4/2012 | Kokoris et al. | |
| 2012/0115736 | A1 | 5/2012 | Bjornson et al. | |
| 2013/0092541 | A1 | 4/2013 | Drndic et al. | |
| 2013/0256118 | A1 | 10/2013 | Meller et al. | |
| 2013/0264207 | A1 | 10/2013 | Ju et al. | |
| 2014/0024125 | A1 | 1/2014 | Golovchenko et al. | |

FOREIGN PATENT DOCUMENTS

| WO | 2013119784 | | 8/2013 |
|---|---|---|---|
| WO | 2013123379 | A2 | 8/2013 |
| WO | 2013/191793 | A1 | 12/2013 |
| WO | 2013185137 | | 12/2013 |

OTHER PUBLICATIONS

Branton D.; Deamer, D. W.; Marziali, A.; Bayley, H.; Benner, S. A.; Butler, T.; Di Ventra, M.; Garaj, S.; Hibbs, A.; Huang, X.; et al. The Potential and Challenges of Nanopore Sequencing. Nat. Biotechnol. 2008, 26, 1146-1153.

Nivala J.; Marks, D. B.; Akeson, M. Unfoldase-Mediated Protein Translocation through an Alpha-Hemolysin Nanopore. Nat. Biotechnol. 2013, 31, 247-250.

Shasha C.; Henley, R. Y.; Stoloff, D. H.; Rynearson, K. D.; Hermann, T.; Wanunu, M. Nanopore-Based Conformational Analysis of a Viral RNA Drug Target. ACS Nano 2014, 8, 6425-6430.

Keyser U. F.; Koeleman, B. N.; Van Dorp, S.; Krapf, D.; Smeets, R. M. M.; Lemay, S. G.; Dekker, N. H.; Dekker, C. Direct Force Measurements on DNA in a Solid-State Nanopore. Nat. Phys. 2006, 2, 473-477.

Li W.; Bell, N. A. W.; Hemandez-Ainsa, S.; Thacker, V. V.; Thackray, A. M.; Bujdoso, R.; Keyser, U. F. Single Protein Molecule Detection by Glass Nanopores. ACS Nano 2013, 7, 4129-4134.

McNally B.; Singer, A.; Yu, Z. L.; Sun, Y. J.; Weng, Z. P.; Meller, A. Optical Recognition of Converted DNA Nucleotides for Single-Molecule DNA Sequencing Using Nanopore Arrays. Nano Lett. 2010, 10, 2237-2244.

Ando G.; Hyun, C.; Li, J. L.; Mitsui, T. Directly Observing the Motion of DNA Molecules near Solid-State Nanopores. ACS Nano 2012, 6, 10090-10097.

Krishnakumar P.; Gyarfas, B.; Song, W. S.; Sen, S.; Zhang, P. M.; Krstic, P.; Lindsay, S. Slowing DNA Trans Location through a Nanopore Using a Functionalized Electrode. ACS Nano 2013, 7, 10319-10326.

Maitra R. D.; Kim, J.; Dunbar, W. B. Recent Advances in Nanopore Sequencing. Electrophoresis 2012, 33, 3418-3428.

Demuro A.; Parker, I. Imaging the Activity and Localization of Single Voltage-Gated Ca2+ Channels by Total Internal Reflection Fluorescence Microscopy. Biophysical Journal 86(5) 3250-3259, 2004.

Manrao E. A.; Derrington, I. M.; Laszlo, A. H.; Langford, K. W.; Hopper, M. K.; Gillgren, N.; Pavlenok, M.; Niederweis, M.; Gundlach, J. H. Reading DNA at Single-Nucleotide Resolution with a Mutant Mspa Nanopore and Phi29 DNA Polymerase. Nat. Biotechnol. 2012, 30, 349-353.

Heron A. J.; Thompson, J. R.; Cronin, B.; Bayley, H.; Wallace, M. I. Simultaneous Measurement of Ionic Current and Fluorescence from Single Protein Pores. J. Am. Chem. Soc. 2009, 131, 1652-1653.

Keyser U. F.; Krapf, D.; Koeleman, B. N.; Smeets, R. M. Dekker, N. H.; Dekker, C. Nanopore Tomography of a Laser Focus. Nano Lett. 2005, 5, 2253-2256.

Di Fiori N.; Squires, A.; Bar, D.; Gilboa, T.; Moustakas, T. Meller, A. Optoelectronic Control of Surface Charge Translocation Dynamics in Solid-State Nanopores. Nat. Nano 2013, 8, 946-951.

Wanunu M.; Dadosh, T.; Ray, V.; Jin, J.; McReynolds, Drndic, M. Rapid Electronic Detection of Probe-Specific Micromas Using Thin Nanopore Sensors. Nat. Nanotechnol. 2010, 5, 807-814.

Smeets R et al. Noise in solid-state nanopores. PNAS 2008, 105, 417-421.

Ayub et al. Nanopore-Based Identification of Individual Nucleotides for Direct RNA Sequencing. Nano Lett. 2013, 13, 6144-6150.

M. Wanunu, "Nanopores: A journey towards DNA sequencing", Phys. Life Rev., May 2012, vol. 9, No. 2, pp. 125-158.

S. Howarka, et al., "Nanopore analytics: sensing of single molecules", Chemical Society Reviews, (2009), vol. 38, No. 8, p. 2360-2384.

U. F. Keyser, "Controlling molecular transport through nanopores", J. R. Soc. Interface, (2011), vol. 8, pp. 1369-1378.

* cited by examiner

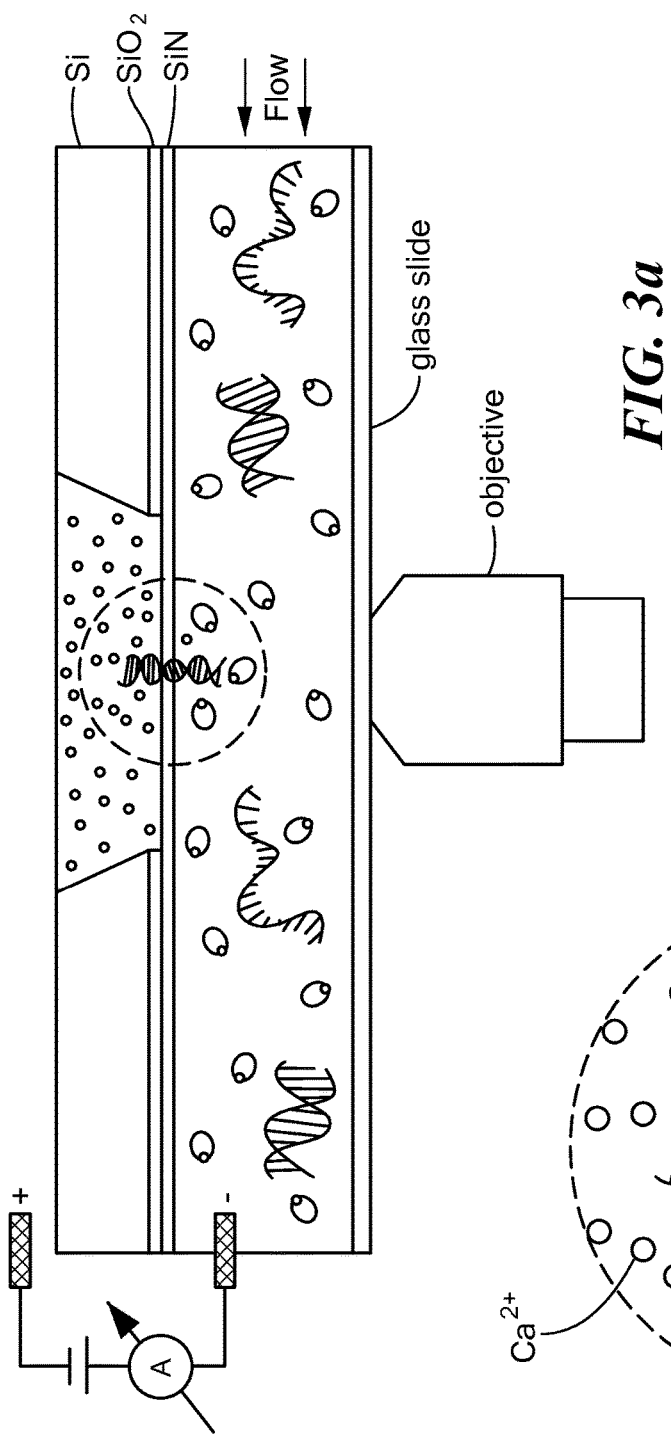
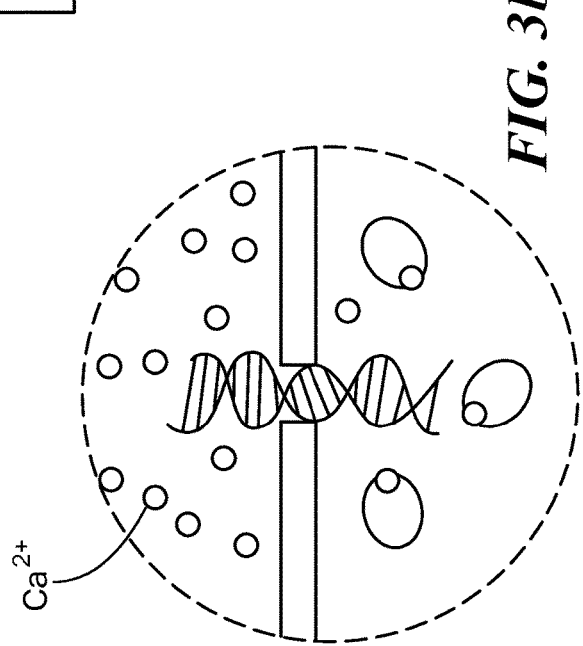
FIG. 3a
FIG. 3b

Fluo-4: X = F, R = Me   Fluo-8: X = H, R = H

— Simultaneous detection of events optically
— Simultaneous detection of events electrically

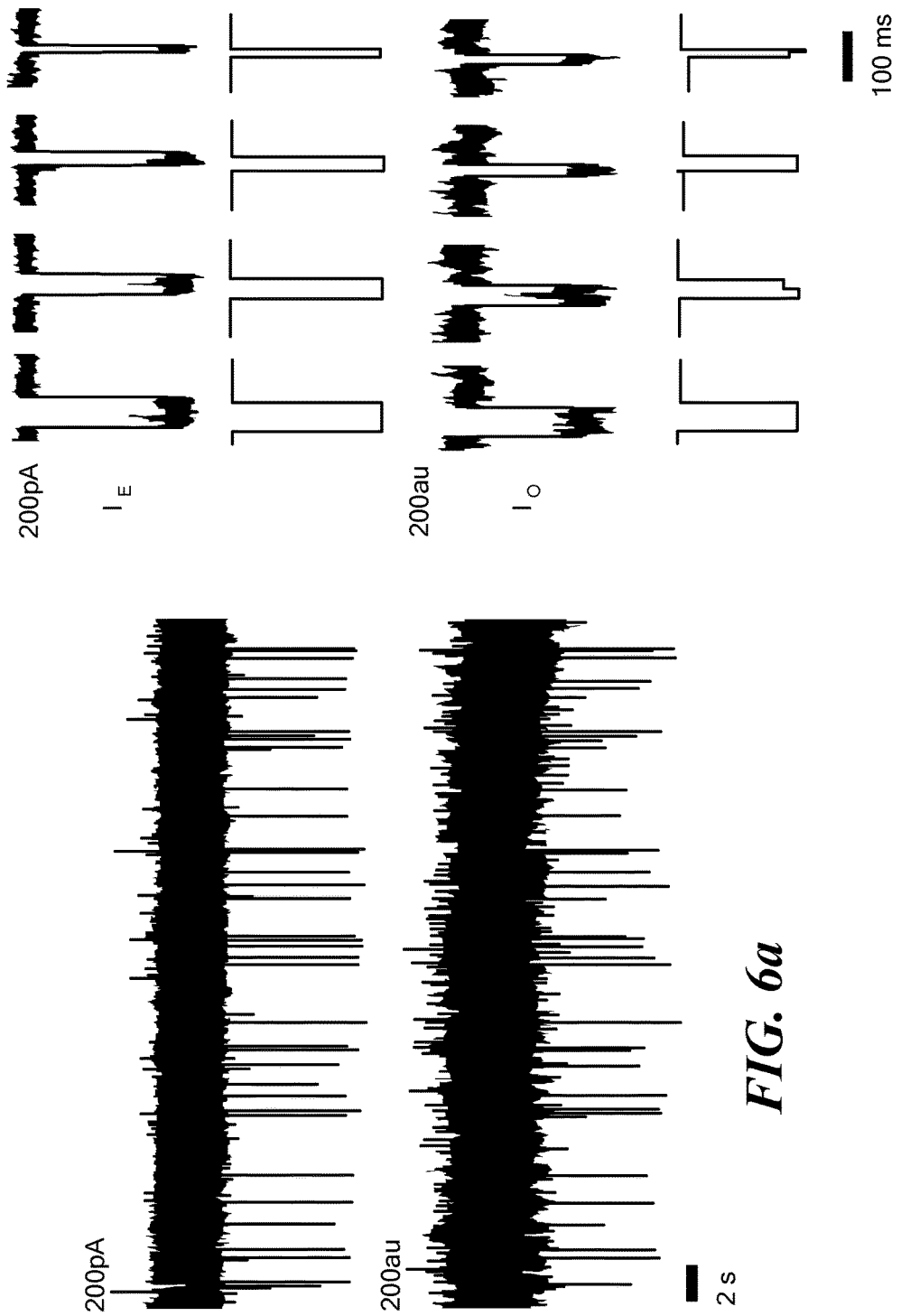

FLUORESCENCE-BASED ANALYSIS OF BIOPOLYMERS USING NANOPORES

CROSS REFERENCE TO RELATED APPLICATIONS

This application claims the benefit of U.S. Provisional Application No. 61/942,772 filed Feb. 21, 2014 and entitled "Label-free fluorescence-based biopolymer sequencing using nanopore arrays", which is hereby incorporated by reference in its entirety.

STATEMENT REGARDING FEDERALLY SPONSORED RESEARCH OR DEVELOPMENT

This invention was developed with financial support from Grant Nos. R21-HG006873 and R01-HG006321 from the National Institutes of Health and from Grant No. ECCS-0335765 from the National Science Foundation. The U.S. Government has certain rights in the invention.

BACKGROUND

Nanopores offer a unique capability of sensing and manipulating single molecules in a label-free manner. In a typical nanopore measurement, an insulating membrane separates two chambers containing an electrolyte solution, and analyte molecules in the solution are electrophoretically driven across the barrier via a nanometer-scale aperture contained in the membrane. A characteristic transient drop in the ionic conductance of the pore is observed for each passing molecule, which is used to determine its identity. Over the past decade, nanopore-based techniques have been suggested for a wide range of biophysical and biomedical applications, including DNA sequencing,[1,2] RNA sequencing,[3] protein sequencing,[4-6] drug discovery;[7] single-molecule biophysics;[8,9] and proteomics.[10-13]

Due to the stochastic nature of single-molecule detection using nanopores, many discrete molecular observations are required in order to obtain statistically significant data for a sample. Multiplexed detection from an array of sensors can considerably speed up measurements, thereby reducing the molecular/biological sample requirement. Furthermore, the ability to introduce sensors tailored for different molecules on a single device can afford complex mixture analysis at unprecedentedly small volumes. However, a critical requirement for this is that each pore in the sensor array is monitored independently, which in the case of electrical detection requires advanced microfluidics and integrated circuitry. Indeed, various schemes have been proposed and demonstrated for multiplexed detection, which include optical approaches,[14-19] field effect/tunneling based detection,[20-26] and fluid wells connected to electrode arrays.[27-29] Nonoptical approaches to reading multiple pores, namely, tunneling-based or fluid wells, are both limited by the need for a network of parallel electrodes and/or fluid conduits that lead to macroscale contacts. On-board amplifiers can alleviate the space requirements of integration, although a recent review estimated that a cost-effective integration would be limited to 1000 amplifiers in a 600 mm² chip area.[30] For comparison, in the Ion Torrent device, a similar sized chip can accommodate a million measurement chambers, three orders-of-magnitude higher than on-board amplified nanopore circuits. Moreover, such nanopore array systems are comprised of two array chips that require alignment, one for circuitry and another for fluidics. Therefore, despite recent demonstrations of devices with arrays of 16 R-hemolysin nanopores,[27] 16 glass nanopore channels,[28] and an 8-channel R-hemolysin platform,[29] scaling up of the nanosensor and its readout is more space-consuming than the sensor itself.

In contrast, optical methods for multiplexed detection have made it possible to simultaneously observe optical signals in nanopores using labeled molecules.[14-19] However, the need for labeling the sample is restrictive, and detection is plagued with false negatives due to sample bleaching and imperfect labeling. Recently, a method was developed for monitoring ion flow through individual protein channels.[32-34] In this method, $Ca^{2+}$-sensitive fluorescent dyes are used to monitor changes in $Ca^{2+}$ concentration in the immediate vicinity of membrane channels. Theoretical studies on ion channels have suggested that $Ca^{2+}$-based approaches can yield signal-to-noise ratios>10:1 at a millisecond time resolution.[35] Parallel optical readout of multipore ionic currents at these time resolutions is attractive for emerging nanopore applications, particularly for enzyme-driven DNA sequencing applications.[36-39] For these reasons, this approach has been used for localizing and imaging ionic current through multiple ion channel proteins simultaneously.[40] Although this appears to be a viable strategy for parallelization of nanopore measurements, the only attempt to utilize the fluorescent sensing of ionic current through nanopores was made by Heron and co-workers.[41] However, this study provided only limited insight into the feasibility of the optical detection of ionic current in nanopore experiments, as no biomolecular translocation data were reported, optical imaging was performed at only 100 fps, and the high $Ca^{2+}$ concentrations used were incompatible with most enzymatic applications. Finally, the approach was limited to lipid-embedded protein channels in a total-internal reflection fluorescence (TIRF) mode, which sets restrictions on the pore size range and the geometry of the setup.

Accordingly, there is a need for systems and methods that allow detection of ion flux through nanopores as a means of analyzing biopolymers. In particular, it would be advantageous for such systems and methods to avoid a requirement for electrically monitoring ionic currents at each pore of the device.

SUMMARY OF THE INVENTION

Described herein are systems for analysis of biopolymers and complexes containing biopolymers based on optical measurement of ion flux through pores. Also described are methods of using such devices for analysis of biopolymers and complexes containing biopolymers, including methods of determining the nucleotide sequences of polynucleotides.

In one aspect, the invention is a system for analyzing a biopolymer or complex containing a biopolymer, the system including: a first reservoir containing an electrically conductive aqueous solution containing a fluorescent reporter molecule capable of producing a fluorescence emission that is altered in the presence of an ionic species; an electrode disposed within the first reservoir in electrical contact with the electrically conductive aqueous solution; a second reservoir containing an electrically conductive aqueous solution containing the ionic species; another electrode disposed within the second reservoir and in electrical contact with the electrically conductive aqueous solution; and a membrane separating the two reservoirs, the membrane having a pore through which members of the ionic species can pass.

The biopolymer may be a polynucleotide, e.g., a DNA or RNA molecule, a polypeptide, or a polysaccharide. In some embodiments, the biopolymer is a polynucleotide. In some embodiments, the biopolymer is DNA. In some embodiments, the biopolymer is RNA. The polynucleotide may be single-stranded or double-stranded, or it may have both single-stranded and double-stranded portions. In some embodiments, the polynucleotide has at least one end that is single-stranded. In some embodiments, the single-stranded end of the polynucleotide has a free 5' phosphate group. In some embodiments, the polynucleotide is a primed single-stranded template. The complex containing the biopolymer may include a polynucleotide and a protein or a polynucleotide and an enzyme.

The fluorescent reporter molecule may be any molecule that produces a fluorescence emission that is altered in the presence of an ionic species. For example, the fluorescent reporter molecule may bind to an ion and produce different fluorescence emission when bound to the ion. For example, the fluorescence emission may increase or decrease when the fluorescent reporter molecule is bound to the ion, or the peak wavelength of the emission spectrum may shift when the fluorescent reporter molecule is bound to the ion. In some embodiments, the fluorescent reporter molecule is Indo-1, Fluo-3, Fluo-4, Fluo-8, DCFH, DHR, or SNARF. In some embodiments, the ionic species is $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $Cr^{3+}$, $Cu^+$, $Cu^{2+}$, $Dy^{3+}$, $Eu^{3+}$, $Fe^{2+}$, $Fe^{3+}$, $Ga^{3+}$, $H^+$, $Hg^+$, $Hg^{2+}$, $In^{3+}$, $La^{3+}$, $Mn^{2+}$, $Mo^{3+}$, $Ni^{2+}$, $OH^-$, $Pb^{2+}$, $Pd^{2+}$, $Pt^{2+}$, $Pt^{4+}$, $Ru^{3+}$, $Sb^{3+}$, $Sc^{3+}$, $Sn^{2+}$, $Sr^{2+}$, $Tb^{3+}$, $Tl^+$, or $Zn^{3+}$.

In some embodiments, the pore has a diameter of about 0.3 nm, about 0.4 nm, 0.5 nm, about 0.6 nm, about 0.7 nm, about 0.8 nm, about 0.9 nm, about 1 nm, about 1.5 nm, about 2 nm, about 3 nm, about 4 nm, about 5 nm, about 6 nm, about 7 nm, about 7.5 nm, about 8 nm, about 10 nm, about 12 nm, about 15 nm, about 20 nm, about 25 nm, about 30 nm, about 35 nm, about 40 nm, about 45 nm, or about 50 nm. In some embodiments, the pore has a diameter from about 0.5 to about 50 nm, from about 1 to about 50 nm, from about 2.5 to about 50 nm, from about 5 to about 50 nm, from about 10 to about 50 nm, from about 0.5 to about 20 nm, from about 0.5 to about 10 nm, from about 0.5 to about 5 nm, from about 0.3 to about 5 nm, from about 1 to about 5 nm, from about 1 to about 3 nm, or from about 0.5 to about 2.5 nm.

In some embodiments, the pore has a longitudinal length of about 0.2 nm, 0.3 nm, 0.4 nm, 0.5 nm, about 0.6 nm, about 0.7 nm, about 0.8 nm, about 0.9 nm, about 1 nm, about 1.5 nm, about 2 nm, about 2.7 nm, about 3 nm, about 4 nm, about 5 nm, about 6 nm, about 7 nm, about 7.5 nm, about 8 nm, about 10 nm, about 12 nm, about 15 nm, about 20 nm, about 25 nm, about 30 nm, about 35 nm, about 40 nm, about 45 nm, or about 50 nm. In some embodiments, the pore has a longitudinal length of from about 0.5 to about 50 nm, from about 1 to about 50 nm, from about 2.5 to about 50 nm, from about 5 to about 50 nm, from about 10 to about 50 nm, from about 0.5 to about 20 nm, from about 0.5 to about 10 nm, from about 0.5 to about 5 nm, from about 1 to about 5 nm, from about 1 to about 3 nm. of from about 0.3 to about 2.5 nm.

The membrane may be made of any ion-insulating material. In some embodiments, the membrane is made of solid-state material. In some embodiments, the membrane is made of silicon, silicon nitride, silicon dioxide, mica, hafnium oxide, molybdenum disulfide, or polyimide.

In some embodiments, the solution in the first reservoir contains the biopolymer or a complex containing the biopolymer. In some embodiments the solution in the first reservoir contains a polynucleotide polymerase or a helicase. In some embodiments, the solution in the first reservoir contains at least four deoxyribonucleotide polyphosphate (dNPP) analogs, wherein incorporation of each dNPP analog during DNA strand synthesis by the polynucleotide polymerase results in release of a different polyphosphate-tag moiety. In some embodiments, the solution in the first reservoir contains two or more different types of nucleotide analogs, each containing a current blockade label attached to the phosphate portion of the nucleotide analogs such that the current blockade label is cleaved upon incorporation of the nucleotide into a growing strand.

In some embodiments, the solution in the second reservoir contains the biopolymer or a complex containing the biopolymer. In some embodiments the solution in the second reservoir contains a polynucleotide polymerase or a helicase. In some embodiments, the solution in the second reservoir contains at least four deoxyribonucleotide polyphosphate (dNPP) analogs, wherein incorporation of each dNPP analog during DNA strand synthesis by the polynucleotide polymerase results in release of a different polyphosphate-tag moiety. In some embodiments, the solution in the second reservoir contains two or more different types of nucleotide analogs, each containing a current blockade label attached to the phosphate portion of the nucleotide analogs such that the current blockade label is cleaved upon incorporation of the nucleotide into a growing strand.

In some embodiments, the membrane has a molecular motor, e.g., an enzyme, immobilized in a region proximal to the pore. In some embodiments, the molecular motor, e.g., enzyme is on the side of the membrane in contact with the first electrically conductive aqueous solution containing the fluorescent reporter molecule. In some embodiments, the molecular motor, e.g., enzyme is on the side of the membrane in contact with the second electrically conductive aqueous solution containing the ion that binds to the fluorescent reporter molecule. The molecular motor, e.g., enzyme, may be less than 10 nm, less than 20 nm, less than 30 nm, less than 40 nm, less than 50 nm, less than 75 nm or less than 100 nm, from the edge of the pore, or from about 1 nm to about 100 nm, from about 2 nm to about 50 nm, or from about 2 nm to about 20 nm from the edge of the pore. The enzyme may be a DNA polymerase, RNA polymerase, DNA exonuclease, RNA exonuclease, DNA translocase, RNA translocase, peptide translocase, ribosome, DNA helicase, or RNA helicase.

In some embodiments, transit of a portion of the biopolymer through the pore impedes passage of ions through the pore. In some embodiments, the portion of the biopolymer that passes through the pore is a single-stranded polynucleotide, a double-stranded polynucleotide, or an unfolded polypeptide. In some embodiments, transit of ribonucleotides, deoxyribonucleotides, or analogs thereof through the pore impedes passage of ions through the pore. In some embodiments, deoxyribonucleotide polyphosphate (dNPP) analogs pass through the pore. In some embodiments, transit of deoxyribonucleotide polyphosphate (dNPP) analogs or nucleotide analogs containing current blockade labels through the pore impedes passage of ions through the pore.

In some embodiments, the system includes a light source capable of illuminating a region of the membrane proximal to the pore. For example, the light source may illuminate a region about 10 μm, about 20 μm, about 50 μm, about 100 μm, about 200 μm, or about 500 μm in diameter. In some embodiments the light source provides light within a specified range of wavelengths. In some embodiments, the light source illuminates a region on one side of the membrane.

In some embodiments, the system includes a light sensor capable of detecting an optical signal in a region of the membrane proximal to the pore. In some embodiments, the light sensor is a microscopic imaging system, a photomultiplier, or a photodiode.

In some embodiments, the membrane contains a plurality of pores. For example, the membrane may have at least 5, at least 10, at least 20, at least 50, at least 100, at least 200, at least 500, at least 1000, at least 2000, at least 5000, at least 10,000, at least 20,000, at least 50,000 or at least 100,000 pores.

In some embodiments, the system has multiple membranes, and each membrane has multiple pores. For example, the system may have at least 5, at least 10, at least 20, at least 50, at least 100, at least 200, at least 500, at least 1000, at least 2000, at least 5000, at least 10,000, at least 20,000, at least 50,000 or at least 100,000 pores.

In another aspect, the invention includes a method of obtaining information about the structure of biopolymer, the method comprising the steps of: providing a system of the invention containing the biopolymer or biopolymer complex in the first reservoir; applying a light signal capable of exciting the fluorescent reporter molecule to a region in the first reservoir proximal to the pore; applying an electric field between the first and second electrodes, the electric field causing (1) members of the ionic species to pass through the pore from the second reservoir to the first reservoir and bind to the fluorescent reporter molecule, thereby producing a change in the fluorescence emission from the fluorescent reporter molecule and (2) a portion of the biopolymer to pass through the pore from the first reservoir to the second reservoir, whereby transit of members of the ionic species through the pore is altered in a manner dependent on the structure of the biopolymer, thereby causing a change in the fluorescence emission from the fluorescent reporter molecule, and measuring the fluorescent signal to obtain information about the structure of the biopolymer.

In some embodiments, the biopolymer is a polynucleotide. In some embodiments, the portion of the polynucleotide that passes through the pore is single-stranded DNA, single-stranded RNA, double-stranded DNA, or double stranded RNA. In some embodiments, the information about the structure of polynucleotides in the nucleotide sequence, the presence or absence of chemical modifications, e.g., methylation of bases, or binding of the polynucleotide to other molecules, e.g., polypeptides.

In some embodiments, the biopolymer is a polypeptide. In some embodiments, the portion of the polypeptide that passes through the pore is a portion of the unfolded polypeptide. In some embodiments the information about the polypeptide is the amino acid sequence, secondary structural features, (e.g., the presence or absence of α-helices, β-strands, β-sheets, β-barrels, etc.), tertiary features (e.g., globular domains, coiled-coil domains, enzymatic domains, etc.), binding to other molecules (e.g., polynucleotides, other polypeptides, etc.), or covalent modifications (e.g., phosphorylation, prenylation, myristoylation, thioacylation, cholesterol modification, glycyophosphatidylinositol linkage, palmitoylation, glycosylation, etc.)

In another aspect, the invention includes a method of determining the nucleotide sequence of a polynucleotide, the method including the steps of: providing a system of the invention, wherein the membrane has a polynucleotide polymerase immobilized within 100 nm of the pore and in electrical contact with the second electrically conductive aqueous solution, and wherein the second electrically conductive solution in the second reservoir contains (1) two or more different types of nucleotide analogs, each containing a current blockade label attached to the phosphate portion of the nucleotide analogs such that the current blockade label is cleaved upon incorporation of the nucleotide into a growing strand, and (2) the polynucleotide, wherein the polynucleotide is a primed single-stranded template; allowing the polynucleotide polymerase to form a complex with the primed single-stranded template; allowing the polynucleotide polymerase to mediate nucleic acid synthesis using the two or more different types of nucleotide analogs containing current blockade labels; applying a light signal capable of exciting the fluorescent reporter molecule to a region in the first reservoir proximal to the pore; applying an electric field between the first and second electrodes, the electric field causing (1) members of the ionic species to pass through the pore from the second reservoir to the first reservoir and bind to the fluorescent reporter molecule, thereby producing a change in the fluorescence emission from the fluorescent reporter molecule, and (2) the current blockade labels to pass through the pore from the from the second reservoir to the first reservoir, whereby transit of members of the ionic species through the pore is reduced and the change in the fluorescence emission from the fluorescent reporter molecule is attenuated differently by each current blockade label; and measuring the fluorescent signal so as to determine the nucleotide sequence of the polynucleotide.

In another aspect, the invention includes a method of determining the nucleotide sequence of a polynucleotide, the method including the steps of: providing a system of the invention, wherein the membrane has a polynucleotide polymerase immobilized within 100 nm of the pore and in electrical contact with the first electrically conductive aqueous solution, and wherein the first electrically conductive solution contains (1) at least four deoxyribonucleotide polyphosphate (dNPP) analogs, wherein incorporation of each dNPP analog during DNA strand synthesis by the polynucleotide polymerase results in release of a different polyphosphate-tag moiety, and (2) the polynucleotide, wherein the polynucleotide is a primed single-stranded template; allowing the polynucleotide polymerase to form a complex with the primed single-stranded template; allowing the polynucleotide polymerase to mediate nucleic acid synthesis using the at least four deoxyribonucleotide polyphosphate (dNPP) analogs; applying a light signal capable of exciting the fluorescent reporter molecule to a region in the first reservoir proximal to the pore; applying an electric field between the first and second electrodes, the electric field causing (1) members of the ionic species to pass through the pore from the second reservoir to the first reservoir and bind to the fluorescent reporter molecule, thereby producing a change in the fluorescence emission from the fluorescent reporter molecule, and (2) the current blockade labels to pass through the pore from the from the second reservoir to the first reservoir, whereby transit of members of the ionic species through the pore is reduced and the change in the fluorescence emission from the fluorescent reporter molecule is attenuated differently by each current blockade label; and measuring the fluorescent signal so as to determine the nucleotide sequence of the polynucleotide.

In another aspect, the invention includes a method of determining the nucleotide sequence of a polynucleotide, the method including the steps of: providing a system of the invention, wherein the first electrically conductive solution contains (1) a polynucleotide polymerase and (2) the polynucleotide, wherein the polynucleotide is a primed single-stranded template; allowing the polynucleotide polymerase to form a complex with the primed single-stranded template; applying a light signal capable of exciting the fluorescent reporter molecule to a region in the first reservoir proximal to the pore; applying an electric field between the first and second electrodes, the electric field causing (1) members of the ionic species to pass through the pore from the second reservoir to the first reservoir and bind to the fluorescent reporter molecule, thereby producing a change in the fluorescence emission from the fluorescent reporter molecule, and (2) the single-stranded portion of the template to pass through the pore from the first reservoir to the second reservoir, thereby causing the complex to be retained in the pore; allowing the polynucleotide polymerase to mediate nucleic acid synthesis, thereby pulling the single-stranded portion of the template through the pore from the second reservoir to the first reservoir, whereby transit of members of the ionic species through the pore is reduced and the change in the fluorescence emission from the fluorescent reporter molecule is attenuated differently for each type of nucleotide in the polynucleotide; and measuring the fluorescent signal so as to determine the nucleotide sequence of the polynucleotide.

In another aspect, the invention includes a method of determining the nucleotide sequence of a polynucleotide, the method including the steps of: providing a system of the invention, wherein the first electrically conductive solution contains (1) a helicase and (2) the polynucleotide, wherein the polynucleotide has a single-stranded portion and a double-stranded portion; allowing the helicase to form a complex with the polynucleotide; applying a light signal capable of exciting the fluorescent reporter molecule to a region in the first reservoir proximal to the pore; applying an electric field between the first and second electrodes, the electric field causing (1) members of the ionic species to pass through the pore from the second reservoir to the first reservoir and bind to the fluorescent reporter molecule, thereby producing a change in the fluorescence emission from the fluorescent reporter molecule; and (2) the single-stranded portion of the polynucleotide to pass through the pore from the first reservoir to the second reservoir, thereby causing the complex to be retained in the pore; allowing the helicase to separate the strands of the double-stranded portion of the polynucleotide, thereby allowing the single-stranded portion to continue to pass through the pore, whereby transit of members of the ionic species through the pore is reduced and the change in the fluorescence emission from the fluorescent reporter molecule is attenuated differently for each type of nucleotide in the polynucleotide; and measuring the fluorescent signal so as to determine the nucleotide sequence of the polynucleotide.

BRIEF DESCRIPTION OF THE DRAWINGS

FIG. 3A is a schematic of a system of the invention being used for analysis of DNA molecules. As $Ca^{2+}$ ions pass through the pore from the upper reservoir to the lower reservoir, they bind to the fluorescent reporter molecule in the lower reservoir, resulting in increased fluorescence emission in the region surrounding the pore. However, when a DNA molecule passes through the pore from the lower reservoir to the upper reservoir, it impedes transit of $Ca^{2+}$ ions, resulting in decreased fluorescence emission in the region surrounding the pore. FIG. 3B is an expanded view of the circled area in FIG. 3A, showing the DNA molecule blocking transit of $Ca^{2+}$ ions through the pore.

FIG. 6A shows continuous electrical (upper) and optical (lower) traces of detected events for 1000 bp dsDNA at 200 mV using 65 mM of $CaCl_2$ in trans and 6.5 µM of Fluo-8 in cis chamber. Optical data was collected at 4.8 kHz and down-sampled to 1 kHz, and electrical data was collected at 20 kHz and low pass filtered to 10 kHz. FIG. 6B shows traces of individual detected events taken from the traces in FIG. 6B (note the difference in time scale between the traces in FIGS. 6A and 6B).

DETAILED DESCRIPTION OF THE INVENTION

The invention provides systems for analyzing biopolymers and complexes containing biopolymers by optical measurement of ion flux through individual pores in a membrane. The system includes two reservoirs separated by the membrane: a first reservoir holds a solution containing a free ionic species, and a second reservoir holds a solution containing a fluorescent reporter molecule whose fluorescence emission is altered by the ionic species. When an electric field is applied, the ionic species passes through the pore from the first reservoir to the second reservoir, a change in the fluorescence emission of the fluorescent reporter molecule is detected. When the pore is partially blocked, however, transit of the ionic species through the pore is impeded, which is measured as a decrease in fluorescence in the vicinity of the pore as compared to the fluorescence resulting from unimpeded flow of the ionic species through the pore. Partial blockage of pore results when another species, such as a portion of a biopolymer or a molecule or portion of a molecule that provides information about the structure or properties of the biopolymer, e.g., a precursor or breakdown product, passes through the pore. The decrease in fluorescence due to partial blockage of the pore correlates with the degree to which ionic transit through pore is impeded, which, in turn, reflects information about the properties of the biopolymer or complex containing a biopolymer.

As used herein, "nanopore" refers to a pore having longitudinal lengths and diameter of less than about 1 µm, for example, from about 0.5 nm to about 999 nm. The term "pore" is agnostic with respect to size and is used interchangeably with "nanopore" in reference to apertures with longitudinal lengths and diameters less than about 1 µm.

Figure 1:
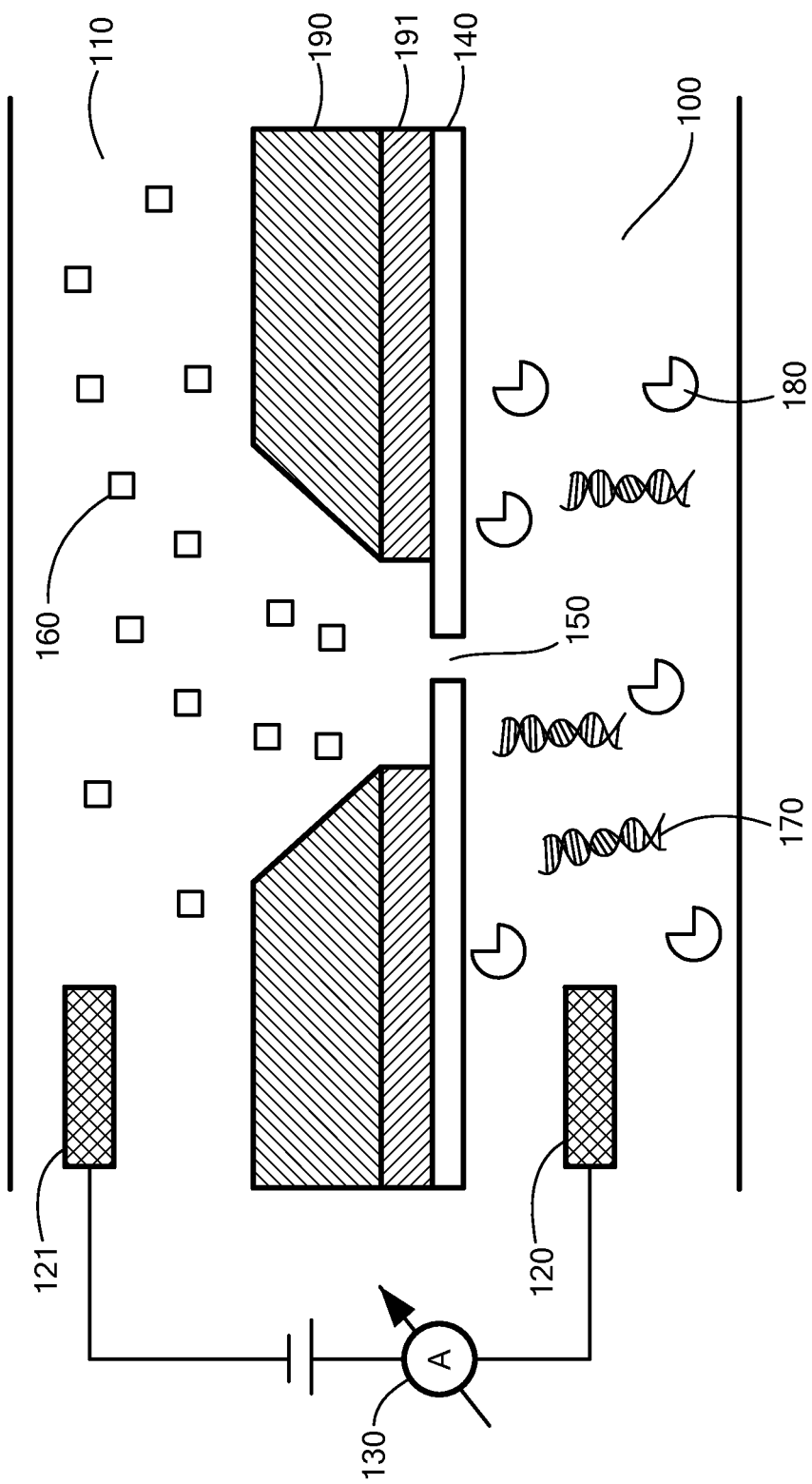
FIG. 1 is a schematic of a system of the invention having one pore as shown in side view.
Figure 2:
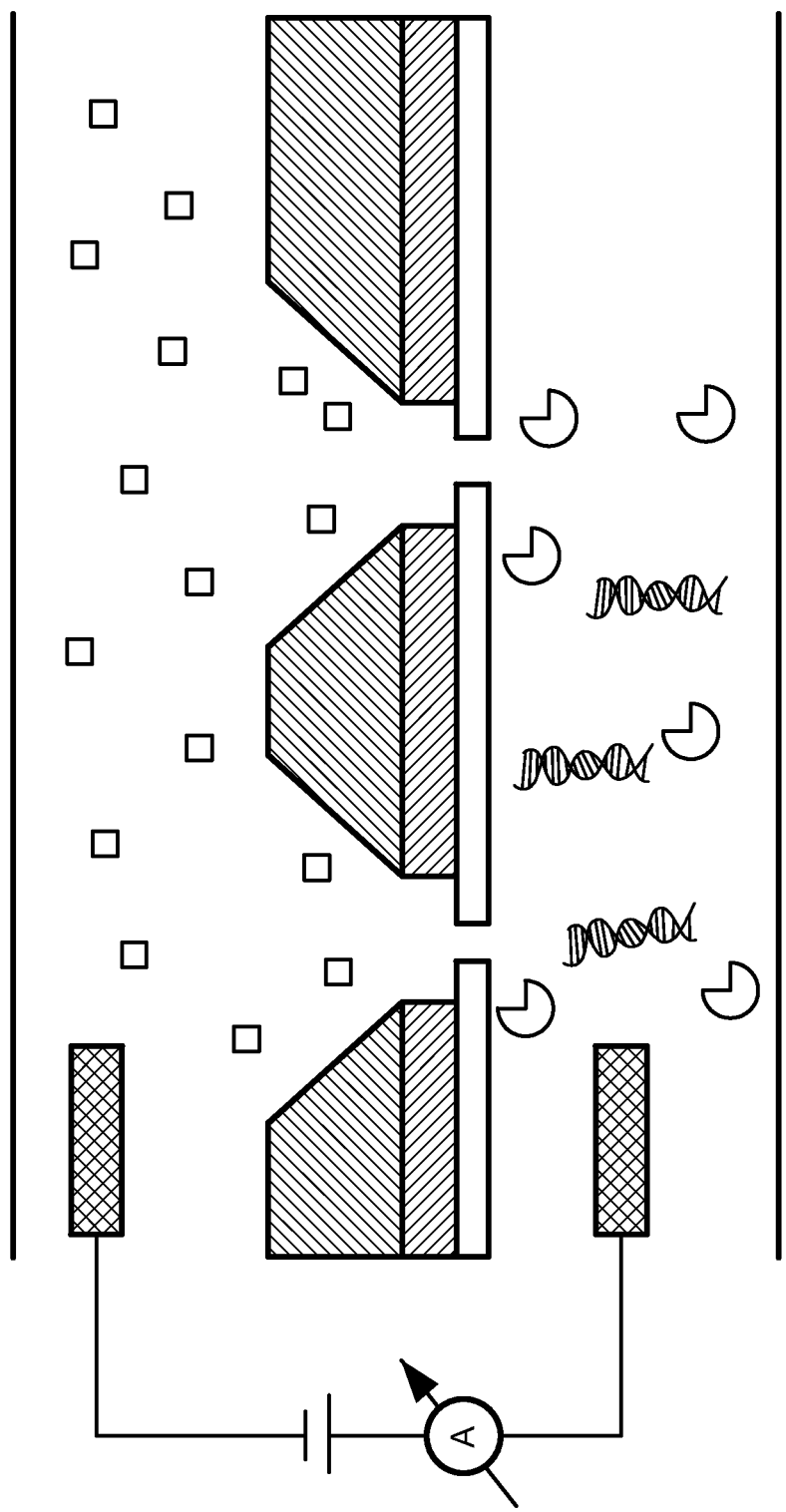
FIG. 2 is a schematic of a system of the invention having multiple pores (two of which are shown) as shown in side view.

A schematic of a system of the invention is shown in FIG. 1. The system includes a first reservoir 100 and second reservoir 110, which are separated by a membrane 140. The first reservoir contains an electrically conductive aqueous solution that contains a fluorescent reporter molecule 180. The second reservoir contains an electrically conductive aqueous solution that contains an ionic species 160 that is capable of producing a change in the fluorescence emission of the fluorescent reporter molecule. In the embodiment shown in FIG. 1, the solution in the first reservoir also contains a biopolymer 170, but it may contain a complex containing the biopolymer. In other embodiments, the biopolymer or biopolymer complex is contained in the solution in the second reservoir. The membrane contains a pore 150 through which the ionic species can pass from the second reservoir to the first reservoir. The system includes a first electrode 120 in electrical contact with the solution in the first reservoir and a second electrode 121 in electrical contact with the solution in the second reservoir. The electrodes are part of an electrical circuit that includes an amplified 130. In the embodiment shown in FIG. 1, the system includes a supporting structure 190 and insulating layer 191.

The system can be used to analyze a biopolymer or biopolymer complex. When an electric potential is applied to the system, the ionic species passes through the pore into the first reservoir, where it triggers a change in the fluorescence emission of the fluorescent reporter molecule. Because passage of the ionic species is limited to the nanopore, this results in a net change in fluorescence in a region proximal to the pore. The intensity of the change in the fluorescent signal in a region proximal to the pore is dependent on the rate of influx of the ionic species into the first reservoir. Consequently, when another species blocks or partially blocks the pore, such as a portion of the biopolymer or biopolymer complex, the change in the fluorescence in the region around the pore is reduced. The reduction in the flow of the ionic species across the pore, and thus the change in the fluorescent signal in a region proximal to the pore, depends on the extent to which transit of the ionic species is blocked. Different species, such as different units of a biopolymer or biopolymer complex, block transit of the ionic species across the pore to a different extent, depending on the size, shape, charge distribution, etc., of the species. Therefore, the magnitude of the change in fluorescence in the region proximal to the pore can be used to identify the blocking species, such as the units of a biopolymer or biopolymer complex, that are passing through the pore.

The system and method encompass any means for blocking or partially blocking the pore the provides information about the biopolymer. For example, a portion of the biopolymer passes through the pore. Different forces may be used to drive a portion of the biopolymer through the pore. For example, the electric potential may drive a portion of the biopolymer through pore in reverse direction from transit of the ionic species, e.g., from the first reservoir to second reservoir in FIG. 1. Alternatively, a portion of the biopolymer may be driven across the pore by mechanical force, e.g., provided by an enzyme (see, e.g., WO 2013/185137) or magnetic force (see, e.g., WO 2013/119784). Alternatively, the species that blocks or partially blocks transit of the ionic species through the pore may be a building block (starting component) for synthesis of a biopolymer, or a portion thereof, or degradation product (breakdown component) of a biopolymer, or a portion thereof. The starting and breakdown components may be synthetic or naturally-occurring. Methods for determining the sequence of a polynucleotide that involve the use of synthetic starting components that are able to block current flow through pores have been described in U.S. Pat. No. 8,652,779 and U.S. 2013/0264207.

The biopolymer may be any biological polymer made of individual units. For example, the biopolymer may be a polynucleotide, e.g., DNA or RNA, polypeptide, or polysaccharide, and the units may be nucleotides, amino acids, or sugar residues, respectively. The polynucleotide may be single-stranded or double-stranded, or it may have a mixture of single-stranded and double-stranded regions. The polynucleotide may be a "primed template" in that it has a primer hybridized to a single-stranded template that can be used by a polynucleotide polymerase to mediate nucleic acid synthesis. The biopolymer may be chemically modified. Examples of chemical modifications of biopolymers include covalent attachment of phosphate (phosphorylation), lipid groups (e.g., prenylation, myristoylation, thioacylation, cholesterol modification, glycyophosphatidylinositol linkage, palmitoylation, etc.) and saccharides (glycosylation) to amino acid residues of polypeptides and covalent attachment of methyl groups (methylation) and other chemical groups to nucleotide bases of DNA.

A biopolymer complex or complex containing a biopolymer refers to any complex that contains at least one biopolymer. A non-limiting list of examples of biopolymer complexes includes protein-DNA complexes, protein-RNA complexes, protein-protein complexes, and RNA-DNA hybrids The pore in the membrane can vary in size depending on the intended application of the system but must be large enough to allow passage of ions of the ionic species used in the system. Preferably, the pore is also small enough to prevent passage of the fluorescent reporter molecule. The pore may be large enough to allow passage of the biopolymer or biopolymer complex. Alternatively, the pore may be large to allow passage of a portion of the biopolymer or biopolymer complex but small enough to prevent passage of the entire biopolymer or biopolymer complex. For example, the pore may allow passage of: single-stranded but not double-stranded polynucleotides; free single-stranded polynucleotides but not single-stranded polynucleotides complexed with polypeptides; natural single-stranded polynucleotides but not modified single-stranded polynucleotides; free double-stranded polynucleotides but not polynucleotides complexed with polypeptides; natural double-stranded polynucleotides but not modified polynucleotides; or unfolded but not folded polypeptides. For example, the pore may have a diameter of about 0.3 nm, about 0.4 nm, 0.5 nm, about 0.6 nm, about 0.7 nm, about 0.8 nm, about 0.9 nm, about 1 nm, about 1.5 nm, about 2 nm, about 3 nm, about 4 nm, about 5 nm, about 6 nm, about 7 nm, about 7.5 nm, about 8 nm, about 10 nm, about 12 nm, about 15 nm, about 20 nm, about 25 nm, about 30 nm, about 35 nm, about 40 nm, about 45 nm, or about 50 nm, or it may have a diameter from about 0.5 to about 50 nm, from about 1 to about 50 nm, from about 2.5 to about 50 nm, from about 5 to about 50 nm, from about 10 to about 50 nm, from about 0.5 to about 20 nm, from about 0.5 to about 10 nm, from about 0.3 to about 5 nm, from about 0.5 to about 5 nm, from about 1 to about 5 nm, from about 1 to about 3 nm, or from about 0.5 to about 2.5 nm. The pore may have a longitudinal length of about 0.2 nm, 0.3 nm, 0.4 nm, 0.5 nm, about 0.6 nm, about 0.7 nm, about 0.8 nm, about 0.9 nm, about 1 nm, about 1.5 nm, about 2 nm, about 2.7 nm, about 3 nm, about 4 nm, about 5 nm, about 6 nm, about 7 nm, about 7.5 nm, about 8 nm, about 10 nm, about 12 nm, about 15 nm, about 20 nm, about 25 nm, about 30 nm, about 35 nm, about 40 nm, about 45 nm, or about 50 nm or it may have a longitudinal length from about 0.5 to about 50 nm, from about 1 to about 50 nm, from about 2.5 to about 50 nm, from about 5 to about 50 nm, from about 10 to about 50 nm, from about 0.5 to about 20 nm, from about 0.5 to about 10 nm, from about 0.5 to about 5 nm, from about 1 to about 5 nm, from about 1 to about 3 nm, from about 0.3 to about 2.5 nm, from about 0.3 to about 1.5 nm, from about 0.3 to about 1 nm, or from about 0.3 to about 0.5 nm.

The membrane may be made of any ion-insulating material. Preferably, the membrane is made of solid-state material. As used herein, "solid-state" refers to any material that exists as a solid at ambient temperatures. For example, membrane may be made of silicon, silicon nitride, silicon dioxide, mica, hafnium oxide, graphene, molybdenum disulfide, or polyimide. Alternatively, the membrane may be made of semi-liquid or liquid crystalline materials, e.g., a lipid bilayer. The membrane may have a uniform thickness. For example, the membrane may be about 0.3 nm, about 0.5 nm, about 0.8 nm, about 1 nm, about 2 nm, about 3 nm, about 4 nm, about 5 nm, about 6 nm, about 8 nm, about 10 nm, about 20 nm, about 40 nm, about 60 nm, about 80 nm, about 100 nm, about 150 nm, about 200 nm, about 300 nm, about 400 nm, about 600 nm, or about 800 nm thick, or it may be from about 0.3 to about 1 nm, about 1 nm to about 3 nm, about 3 nm to about 5 nm, about 5 nm to about 10 nm, about 10 nm to about 800 nm, from about 20 nm to about 800 nm, from about 40 nm to about 800 nm, from about 80 nm to about 800 nm, from about 100 nm to about 800 nm, from about 150 nm to about 800 nm, from about 200 nm to about 800 nm, from about 400 nm to about 800 nm, from about 10 nm to about 400 nm, from about 10 nm to about 200 nm, from about 10 nm to about 100 nm, from about 10 nm to about 80 nm, from about 10 nm to about 40 nm, from about 20 nm to about 400 nm, or from about 80 nm to about 200 nm. Alternatively, the membrane may have a region surrounding the pore that is the thinner than the remainder of the membrane. The thin region may be about 1 nm, about 2 nm, about 5 nm, about 10 nm, about 20 nm, about 40 nm, about 60 nm, about 80 nm, about 100 nm, about 150 nm, about 200 nm, about 300 nm, about 400 nm, or about 600 nm thick, or it may be from about 2 nm to about 400 nm, from about 2 nm to about 200 nm, from about 2 nm to about 100 nm, from about 5 nm to about 400 nm, from about 10 nm to about 100 nm, from about 20 nm to about 100 nm, or from about 10 nm to about 50 nm. The thin region of the membrane facilitates formation of the pore during fabrication of the system. Preferably, the pore is placed in the center of the thin region. Because the thin region of the membrane is substantially larger than the pore and therefore detectable with lower power magnification, the thin region also facilitates spatial orientation of the membrane relative to the light source and light sensor while the system is in use. The thin region, as viewed from a sight line perpendicular to the membrane, may be of any shape. For example, the thin region may be rectangular, square, or circular. The minimum length across the thin region may be about 10 nm, about 20 nm, about 50 nm, about 100 nm, about 200 nm, about 300 nm, about 400 nm, about 500 nm, about 600 nm, about 700 nm, about 800 nm, about 900 nm, or about 1 μm, or from about 10 nm to about 1 μm, from about 20 nm to about 1 μm, from about 50 nm to about 1 μm, from about 100 nm to about 1 μm, from about 200 nm to about 1 μm, or from about 500 nm to about 1 μm.

The pore may be made in the membrane by any method known in the art. For example, the pore may be made by tunneling electron microscopy, He ion beam lithography, or dielectric breakdown. The method of making the pore in the membrane may etch the region surrounding the pore. Consequently, the thin region may itself have variations in thickness, including an area of tapered thickness in proximity of the pore. Thus, the effective longitudinal length of the pore may substantially shorter than the thickest part of the thin region of the membrane. For example, the longitudinal length of the pore may be about 50%, about 25%, about 10%, about 5%, about 2.5%, or about 1% of the maximum thickness of the thin region of the membrane.

The membrane may also be a hybrid of solid-state and two-dimensional liquid materials. For example, the membrane may contain a lipid bilayer within the pore of a solid-state membrane. The lipid bilayer may contain a biological pore, i.e., a pore derived from a biological source. For example, the lipid bilayer may contain a protein pore, such as alpha-hemolysin, MspA porin, and ClyA porin. In such embodiments, the pore in the solid-state portion of the membrane must be large enough to accommodate the biological pore and a surrounding lipid bilayer.

The membrane may be provided as part of a chip that includes a supporting structure, and optionally, an insulating layer. Because the membrane is thin and thus susceptible to being damaged during handling, the supporting structure provides structural strength and rigidity to preserve the integrity of the membrane. The supporting structure may be made of any material and of any thickness suitable for this purpose. For example, the supporting structure may be made of silicon, glass, quartz, sapphire, or mica. The supporting structure may be about 200 μm, about 400 μm, about 500 μm, about 600 μm, about 700 μm, about 800 μm, or about 1 mm thick. An insulating layer may be necessary to electrically insulate the membrane from the supporting structure, so the insulating layer may be made of any material suitable and of any thickness for this purpose. For example, the insulating layer may be made of $SiO_2$, $HfO_2$ or $Al_2O_3$. The insulating layer may be, for example, about 0.5 μm, about 1 μm, about 1.5 μm, about 2 μm, about 2.5 μm, about 3 μm, about 4 μm, about 5 μm, about 6 μm, about 7 μm, about 8 μm, about 9 μm, or about 10 μm thick. To provide access to the membrane, the supporting structure and insulating layer, if present, contain one or more windows in which the membrane is not in contact with the supporting structure or insulating layer. The window, as viewed from a sight line perpendicular to the membrane, may be of any shape. For example, the window may be rectangular, square, or circular. The minimum length across the window must be sufficient to allow access to the region of the membrane, including the thin region if present, containing the pore. For example, the minimum length across the window may be about 1 μm, about 2 μm, about 5 μm, about 10 μm, about 20 μm, about 30 μm, about 40 μm, about 60 μm, about 100 μm, about 120 μm, about 160 μm, or about 200 μm at the site of contact between the window and the substrate.

The fluorescent reporter molecule may be any molecule capable of producing a fluorescence emission that is altered in the presence of an ionic species. For example, the fluorescence emission may increase or decrease when the fluorescent reporter molecule is bound to the ion, or the peak wavelength of the emission spectrum may shift when the fluorescent reporter molecule is bound to the ion. A non-limiting list of fluorescent reporter molecules includes Indo-1, Fluo-3, Fluo-4, Fluo-8, DCFH, DHR, fluorescein and its chemical derivatives, or SNARF.

The ionic species is selected in conjunction with the fluorescent reporter molecule and may be any ionic species that causes a change in the fluorescence emission of another molecule. Examples of ionic species that can alter the fluorescence emission of other molecules include $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $Cr^{3+}$, $Cu^+$, $Cu^{2+}$, $Dy^{3+}$, $Eu^{3+}$, $Fe^{2+}$, $Fe^{3+}$, $Ga^{3+}$, $H^+$, $Hg^+$, $Hg^{2+}$, $In^{3+}$, $La^{3+}$, $Mn^{2+}$, $Mo^{3+}$, $Ni^{2+}$, $OH^-$, $Pb^{2+}$, $Pd^{2+}$, $Pt^{2+}$, $Pt^{4+}$, $Ru^{3+}$, $Sb^{3+}$, $Sc^{3+}$, $Sn^{2+}$, $Sr^{2+}$, $Tb^{3+}$, $Tl^+$, or $Zn^{2+}$.

Detection of fluorescence emission from the fluorescent reporter molecule requires a light source and light sensor. The light source and light sensor may be contained in the same device or in separate devices. The light source must be capable of providing light of a wavelength or range of wavelengths capable of exciting the fluorescent reporter molecule in the presence of the ionic species, and the light sensor must be capable of detecting light of a wavelengths or range of wavelengths emitted by the fluorescent reporter molecule in the presence of the ionic species. The light source may be a laser. The light sensor may be a microscopic imaging system, a photomultiplier, or a photodiode.

The system may include a molecular motor that regulates the rate of transit of the blocking species through the pore. The molecular motor is unable to pass through the pore and may be on the side of the membrane facing the first reservoir or on the side facing the second reservoir. The molecular motor may be an enzyme, for example, a protein or protein complex comprising multiple polypeptides. The molecular motor may be an enzyme that synthesizes, degrades, or alters the structure of the biopolymer being analyzed. For example, the molecular motor may be a DNA polymerase (e.g., phi29), RNA polymerase, DNA exonuclease, RNA exonuclease, DNA helicase, or RNA helicase, a protein unfoldase (e.g., ClpX), or a protein unfoldase/peptidase complex (e.g., ClpXP). The molecular motor may be immobilized on the membrane in a region proximal to the pore, e.g., by a chemical bond that links the molecular motor to the membrane or by a matrix that prevents diffusion of the molecular motor (see, e.g., U.S. Pat. No. 7,238,485). The molecular motor may be less than 10 nm, less than 20 nm, less than 30 nm, less than 40 nm, less than 50 nm, less than 75 nm or less than 100 nm, from the edge of the pore, or from about 1 nm to about 100 nm, from about 2 nm to about 50 nm, or from about 2 nm to about 20 nm from the edge of the pore.

The system may have a membrane containing multiple pores, allowing for simultaneous measurements at different pores. For example, the membrane may have at least 5, at least 10, at least 20, at least 50, at least 100, at least 200, at least 500, at least 1000, at least 2000, at least 5000, at least 10,000, at least 20,000, at least 50,000 or at least 100,000 pores. The system may have multiple membranes, each membrane may have multiple pores. Consequently, the system may have at least 5, at least 10, at least 20, at least 50, at least 100, at least 200, at least 500, at least 1000, at least 2000, at least 5000, at least 10,000, at least 20,000, at least 50,000 or at least 100,000 pores. The system must have sufficient spacing between the pores so that optical measurements at adjacent pores do not interfere with each other. For example, the pores may be spaced at least 100 nm, at least 200 nm, at least 500 nm, at least 1 μm, at least 2 μm, at least 3 μm, at least 4 μm, at least 5 μm, at least 10 μm, or at least 20 μm apart, or they may be spaced from about 100 nm to about 1 μm, from about 200 nm to about 2 μm, from about 400 nm to about 4 μm, from about 500 nm to about 5 μm, or from about 1 μm to about 10 μm apart. The membrane may also have multiple thin regions in which the pores are situated, as described above. Preferably, each thin region has a single pore. Alternatively, multiple pores may be within a single thin region.

The system can be used for various methods of analysis of biopolymers or complexes containing biopolymers. For example, the system can be used for determining the sequence of units within a biopolymer, for example, the sequence of nucleotides within a polynucleotide, e.g., RNA or DNA, or sequence of amino acids within a polypeptide. The system can be used for identifying covalent modifications of units within a biopolymer. For example, the system can be used for identifying methylation of nucleotides within a polynucleotide, e.g., RNA or DNA. The system can be used for measuring binding affinities between biopolymers or between a biopolymer and another molecule within a biopolymer complex. For example, the system can be used for measuring binding affinities between a polynucleotide and polypeptide, between two polynucleotide, or between two polypeptides.

The system can be used for determining the nucleotide sequence of a polynucleotide. Many methods that rely on electrical measurements of current flow through a nanopore to determine the sequence of a polynucleotide have been described in the art. See, e.g., WO 2013/185137, U.S. Pat. No. 8,652,779, U.S. 2013/0264207, WO 2012/088339, U.S. 2007/0190542, WO 2013/119784, and U.S. 2013/0256118. These methods can be readily adapted for use with the system of the present invention to determine the sequence of a polynucleotide by optical measurements.

The sequence of a polynucleotide may be determined using a polynucleotide polymerase as a molecular motor. In one such method, the conductive solution in the first reservoir includes a polynucleotide polymerase and a polynucleotide that has a double-stranded portion and a single-stranded portion, the single-stranded portion having a free 5' phosphate group. The polynucleotide polymerase is allowed to bind to the polynucleotide under conditions that prevent the polymerase from synthesizing a second strand using the single-stranded portion as a template. An electric field is applied to the system, causing the stable polynucleotide-polymerase complex to migrate toward the pore due to the negative charge of the polynucleotide. The single-stranded portion of the polynucleotide enters the pore, but the complex becomes trapped in the pore because the polymerase and double-stranded portion prevent passage of the entire complex. The polymerase is then allowed to synthesize a new strand using the single-stranded portion as a template. The active polymerase pulls the single-stranded portion polynucleotide against the electric field back through the pore into the first reservoir. While the single-stranded portion of the polynucleotide is in the pore, the extent to which each nucleotide unit blocks the flow of ions through the pore depends on the identity of the base of that nucleotide. The transient change in ion flux through the pore is detected as a change in the fluorescence emission of the fluorescent reporter molecule. Therefore, the fluorescence signal can be correlated with the base composition of the strand passing through the pore, and the nucleotide sequence of the polynucleotide can be determined.

The activity of the polynucleotide polymerase may be reversibly inhibited by any method known in the art. For example, the polynucleotide polymerase may be inhibited by low temperature, applied voltage across the nanopore, nucleotide or nucleoside analogs, $Mg^{2+}$ chelators, other small molecules, or any other reversible method. The inhibiting condition is then removed to allow the polynucleotide polymerase to synthesize a new nucleic acid strand.

Alternatively, the polynucleotide polymerase can be immobilized on the membrane in a region proximal to the pore. In one such method, a single copy of the polymerase is immobilized on the side of the membrane facing the second reservoir, as described in detail in U.S. Pat. No. 8,652,779. The solution in the second reservoir contains a primed template for the polynucleotide and at least two, and preferably four, different nucleotide analogs that contain distinct current blockade labels attached to the phosphate portion of the analogs. The primed template forms a complex with the immobilized polymerase, which tethers the primed template to the membrane in a region proximal to the pore, and the polymerase synthesizes a new polynucleotide strand. As each analog becomes incorporated into the growing strand of the polynucleotide, the label from the analog is driven into the pore by the electrical field, where it temporarily blocks transit of the ionic species. When the polymerase cleaves the phosphate portion of the analog to incorporate the nucleotide into the growing strand, the blockade label is released and passes through the pore, allowing unimpeded flow of the ionic species through the pore. Each blockade label is selected to impede flow of the ionic species to a different extent. The extent to which each blockade label impairs transit of ions through the pore is measured as a change in fluorescence emission from the fluorescent reporter molecule. If a separate blockade label is chosen for each of the four naturally occurring nucleotide bases, the sequence of the polynucleotide can be deduced from the changes in fluorescence.

In another method, a complex containing a the polymerase and a primed template for the polynucleotide is immobilized on the side of the membrane facing the first reservoir, as described in detail in U.S. 2013/0264207. Immobilization of the complex may be achieved by immobilization of any of the molecules in the complex individually. For example, the polymerase, the primer, the template, or combinations thereof may be immobilized. The solution in the first reservoir contains at least two, and preferably four, deoxyribonucleotide polyphosphate tags. Each of deoxyribonucleotide polyphosphate tags differs from others by having either (1) a different number of phosphate groups linking the tag to the base of the nucleotide or (2) a different tag. The primed template forms a complex with the immobilized polymerase, which tethers the primed template to the membrane in a region proximal to the pore, and the polymerase synthesizes a new polynucleotide strand. As each deoxyribonucleotide polyphosphate tag becomes incorporated into the growing strand of the polynucleotide, the polymerase cleaves the phosphate portion and the product containing the tag and at least one phosphate group is released. The tag-containing product is driven through the pore by the electrical field, where it transiently impedes flow of the ionic species through the pore. Due to the difference between the tag-containing products in either number of phosphate groups or identity of the tag, each product impedes flow of the ionic species to a different extent, which is measured as a change in fluorescence emission from the fluorescent reporter molecule. The extent to which each product impairs transit of ions through the pore is measured as a change in fluorescence emission from the fluorescent reporter molecule. If a separate deoxyribonucleotide polyphosphate tag is chosen for each of the four naturally occurring nucleotide bases, the sequence of the polynucleotide can be deduced from the changes in fluorescence.

The sequence of a polynucleotide may also be determined using a helicase as a molecular motor. In one such method, the conductive solution in the first reservoir contains a helicase and a polynucleotide that has a double-stranded portion and a single-stranded portion. The helicase is allowed to bind to the polynucleotide under conditions that prevent the helicase from separating the strands of the double-stranded portion of the polynucleotide. An electric field is applied to the system, causing the stable polynucleotide-helicase complex to migrate toward the pore due to the negative charge of the polynucleotide. The single-stranded portion of the polynucleotide enters the pore, but the complex becomes trapped in the pore because the helicase and double-stranded portion prevent passage of the entire complex. The helicase is then allowed to separate the strands of the double-stranded portion of the polynucleotide, which allows the strand in the pore to continue to pass through the pore to the second reservoir due to the electric field. While the single-stranded portion of the polynucleotide is in the pore, the extent to which each nucleotide unit blocks the flow of ions through the pore depends on the identity of the base of that nucleotide. The transient change in ion flux through the pore is detected as a change in the fluorescence emission of the fluorescent reporter molecule. Therefore, the fluorescence signal can be correlated with the base composition of the strand passing through the pore, and the nucleotide sequence of the polynucleotide can be determined.

The activity of the helicase may be reversibly inhibited by any method known in the art. For example, the helicase may be inhibited by low temperature, dibenzothiepins, other small molecules, or any other reversible method. The inhibiting condition is then removed to allow the helicase to synthesize a new nucleic acid strand.

In general, fluorescence-based methods of determining the sequence of a biopolymer, e.g., a polynucleotide, are limited by the rate at which optical images can be captured. Therefore, it is desirable to have a molecular motor, e.g., an enzyme, that processes the biopolymer at a rate similar to the maximum rate of image capturing. Current imaging technologies can capture events as fast as on the order of 0.1-1 ms. Processing rate refers to the number of units of the biopolymer that the molecular motor can process, e.g., add, remove, unwind, separate, transfer, translocate, etc., per unit time. Consequently, the molecular motor, e.g., enzyme, may have a processing rate of about 100-200 Hz, about 100-400 Hz, about 100-800 Hz, about 100-1200 Hz, about 100-1600 Hz, about 100-2000 Hz, about 200-400 Hz, 200-800 Hz, about 200-1200 Hz, about 200-1600 Hz, about 200-2000 Hz, about 400-800 Hz, about 400-1200 Hz, about 400-1600 Hz, about 400-2000 Hz, about 800-1200 Hz, about 800-1600 Hz, about 800-2000 Hz, about 1200-1600 Hz, about 1200-2000 Hz, or 1600-2000 Hz, or higher than that.

For accurate analysis of the biopolymer, the system must be able to detect optically rapid changes in transit of the ion across the pore. Rapid optical detection requires a constant supply of fresh fluorescent reporter molecule in a region proximal to the pore to avoid signal loss due to photobleaching. Because diffusion of the first solution alone may not be sufficient to continuously provide a fresh supply of fluorescent reporter molecule, it is desirable to flow the first solution through at a constant rate. For example, the first solution may be flowed through the first reservoir at a rate of about 5 µl/min, about 10 µl/min, about 20 µl/min, about 50 µl/min, about 100 µl/min, about 200 µl/min, about 500 µl/min, or about 1000 µl/min, or from about 5-10 µl/min, from about 10-20 µl/min, from about 20-50 µl/min, from about 50-100 µl/min, from about 100-200 µl/min, from about 200-500 µl/min, or from about 500-1000 µl/min.

EXAMPLES

Example 1: Materials and Methods

Nanopores were fabricated in ultrathin silicon nitride membranes as described previously.[46] Briefly, a 500-µm-thick silicon wafer with <100> crystal orientation and 2.5 µm of thermal oxide was coated with 100 nm of low-stress chemical vapor deposition silicon nitride (SiN). Standard UV photolithography was used to pattern square openings on one side of the wafer, through which the nitride and oxide were etched using $SF_6$ plasma. The photoresist was stripped, and an anisotropic etch followed by removal of the oxide layer resulted in ~30 µm×30 µm free-standing windows on the reverse side of the wafer.

A film of poly(methyl methacrylate) (PMMA) was spun onto the membrane side of the window, and electron-beam lithography was used to pattern an array of small square openings of 800 nm×800 nm or smaller 1.5-3 µm apart. $SF_6$ plasma etch locally thinned the SiN in these regions to 20 nm to increase the signal while maintaining the membrane's mechanical integrity. The PMMA was removed by incubation in acetone. A single nanopore or an array of nanopores was drilled through the thinned regions (no more than a pore per thinned region) of the SiN membrane using a JEOL 2010F transmission electron microscope. Fabricated pores were 1.5-10 nm in diameter, depending on the application.

The nanopore chip was cleaned in piranha acid using a procedure described previously.[51] After rinsing and drying of the chip, it was immediately mounted onto a custom-designed PEEK fluidic cell using silicone elastomer. The cell contains PEEK screws that allow pressure connection to syringe pumps to enable buffer flow at controlled rates. The silicone was painted over and around the membrane-facing side of the chip leaving <4 mm² area around the membrane, and a piranha-cleaned, rinsed and dried #1 glass coverslip was pressed against the chip. Homemade Ag/AgCl electrodes were immersed in each chamber of the cell and connected to an Axon 200B headstage. All measurements were taken in a dark Faraday cage. Electrical and optical signals were acquired using custom LabVIEW software. The analog current signal from the amplifier was low-pass filtered at 10 kHz and fed to a DAQ card, which sampled the data at 100 kHz/16 bit.

For all experiments, unless otherwise specified, membranes were epi-illuminated by feeding a 20 mW, 488 nm laser power beam (Coherent Sapphire) to the back of an inverted microscope (Olympus IX71) and through an oil immersion high NA objective (Nikon 60×/1.49). High-bandwidth fluorescence detection was achieved using an emCCD camera (Andor, iXon Ultra 897) in crop mode, which allowed frame rates of 2000-4800 frames/s. Synchronization between the electrical and optical signals was achieved by connecting the camera TTL pulse to the main DAQ board (PCI-6630, National Instruments) used for the acquisition of the electrical signal. The fluorophore molecules in the cis chamber were continuously replenished by pumping at a flow rate of 100 µL/min. Custom MATLAB code was used for background subtraction, image filtering, and extraction of fluorescent intensity. Current traces and optical intensity traces were analyzed using the OpenNanopore software[47] to obtain dwell time and current blockage of events.

Example 2: $Ca^{2+}$ Based Epifluorescence Detection of Unlabeled DNA Molecules Using an Array of Solid-State Nanopores A $Ca^{2+}$ dye solution is flowed underneath the membrane using a flow channel, and ion currents are detected through pores as small as 1.8 nm in diameter at millisecond time-resolutions. The spacing between adjacent pores can be as small as a few micrometers, yielding the pore density on a chip comparable to that of Ion Torrent's device and at least 100× higher than any existing nanopore array device. These experiments are performed at $Ca^{2+}$ concentrations in which many biological motors, such as the DNA polymerase φ29 remain active. The ionic current information accessed by optical methods is equivalent to that found electrically, and therefore the method paves the way for large-scale parallelization of a wide range of nanopore measurements.

Figure 3C:
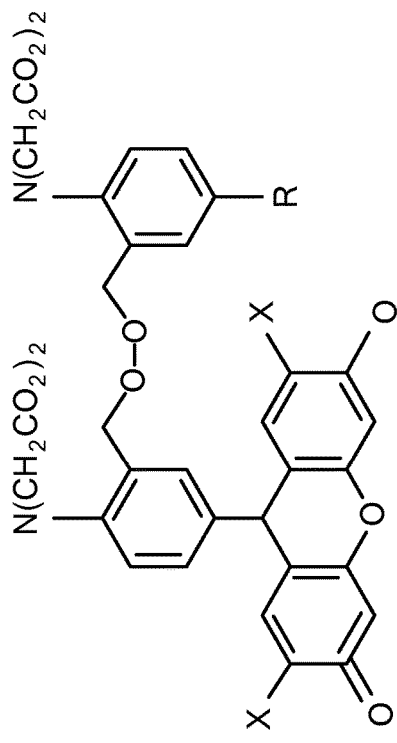
FIG. 3C shows the molecular structure of the fluorescent reporter molecules Fluo-4 and Fluo-8.
Figure 3D:
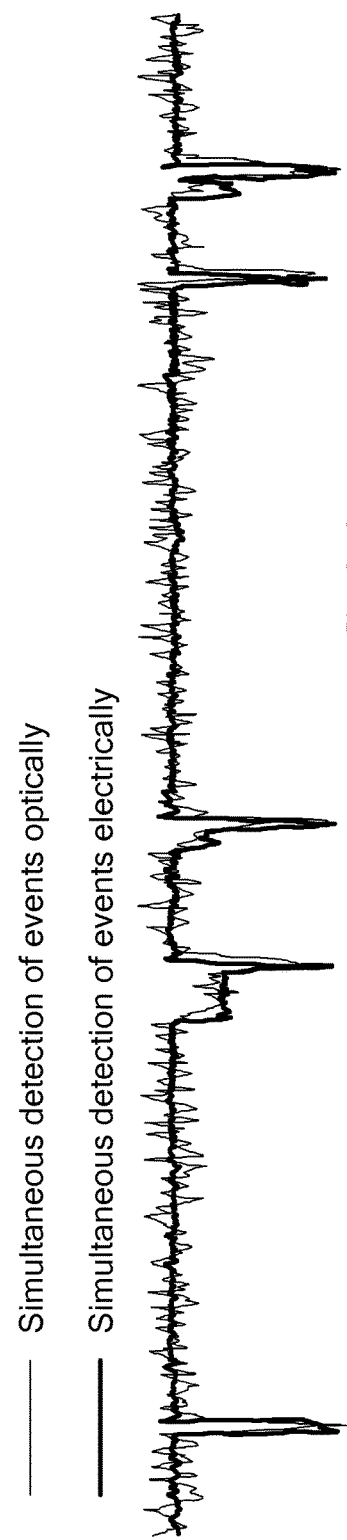
FIG. 3D is graph showing detection of DNA molecules passing through a pore by optical (thin line) and electrical (thick line) measurements.

The system is composed of one or more nanopores formed in a thin insulating silicon nitride membrane, suspended on a silicon chip frame (FIG. 3A, Example 1). The chip is mounted in a custom fluidic cell that permits simultaneous electrical and optical measurements of ionic current through a nanopore. The cell is equipped with channels for embedding Ag/AgCl electrodes on either side of the chip and exchanging buffer on the analyte cis side. To gain optical access to the membrane, the cis side of the chip is covered with a glass coverslip and then the cell is mounted on an inverted microscope with an oil immersion high NA objective (Nikon 60×/1.49). The cis chamber is filled with a solution of 0.4 M KCl, 1 mM EDTA, 65 µM EGTA, 10 mM Tris buffered to pH 7.9, and 6.5 µM of $Ca^{2+}$-sensitive fluorescent dye Fluo-8 (unless otherwise noted) (FIG. 3C). The opposite trans chamber of the cell is filled with a buffer containing 0.4 M KCl, 65 mM $CaCl_2$, and 10 mM Tris buffered to pH 7.9.

This system allows one to apply an electric field across the membrane and electrophoretically drive charged molecules across the pore. The cumulative flow across all pores in the system is monitored electrically by sampling the ionic current across the chip using an Axon Axopatch 200B patch-clamp amplifier. The distinctive feature of this system is the ability to optically monitor the flow of $Ca^{2+}$ ions across each individual pore in parallel. As $Ca^{2+}$ ions are driven across the pore, they form a complex with the calcium sensitive Fluo-8 fluorescent dye molecules. This fluorescent dye is excited by the 488 nm line of an argon-ion laser and exhibits an increase in fluorescent intensity of more than 100× upon binding to $Ca^{2+}$. The flow of $Ca^{2+}$ ions can then be inferred by sampling the fluorescence levels at the site of each nanopore. To reduce background fluorescence, EGTA and EDTA agents are added to the cis chamber to chelate the remaining $Ca^{2+}$ and $Mg^{2+}$ ions.

The intensity of the localized fluorescent signal in the immediate vicinity of each pore is proportional to the $Ca^{2+}$ flux through the pore and remains constant as long as the steady flow of ions and ionophores is maintained. A disruption of the ionic flow due to the presence of an analyte molecule in the pore results in an instantaneous reduction in fluorescence intensity. Thus, this technique optically accesses the same current information as patch-clamp experiments. This implies that all nanopore-based applications that rely on electrical ionic current measurements may be supplanted by optical current measurements. It is noteworthy that the optical readout of the ionic current possesses an advantage over the electrical measurements as it can be scaled up to multiple nanopores with ease. Moreover, in contrast to traditional fluorescent microscopy approaches, this approach is label-free.

Figure 4A:
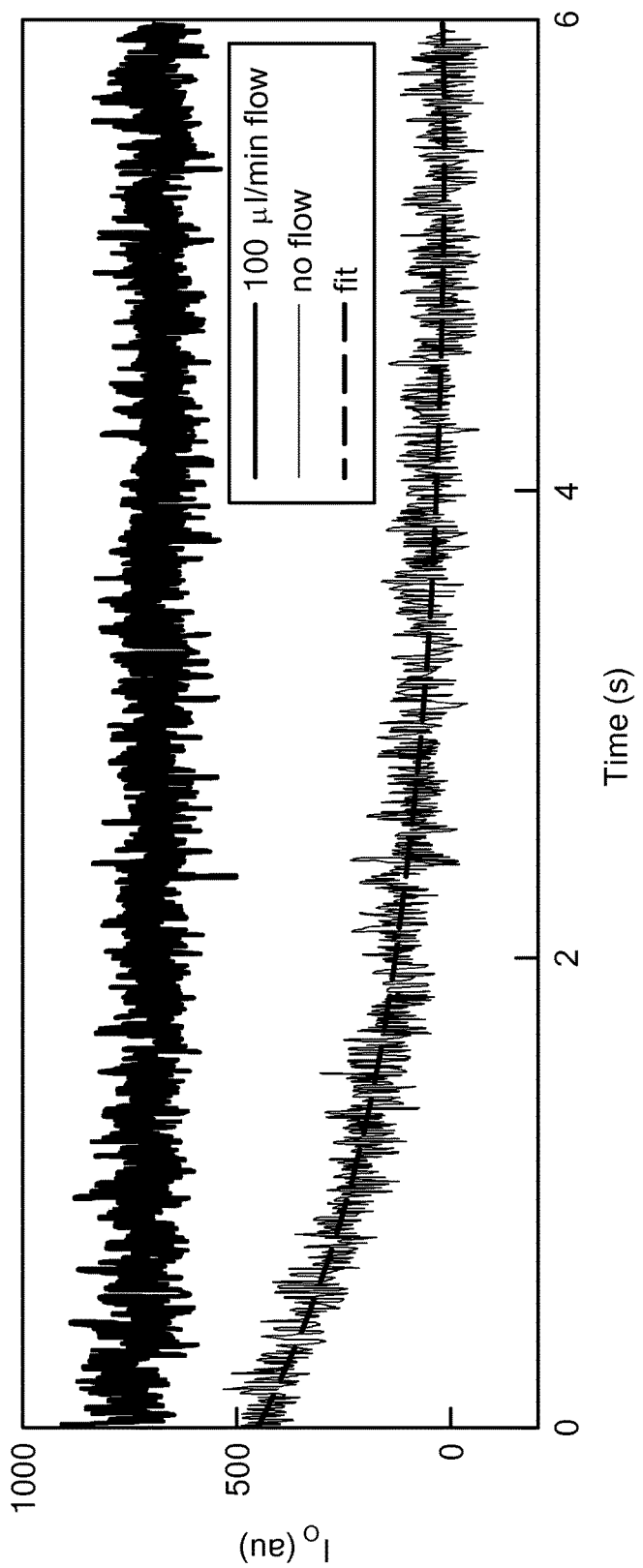
FIG. 4A is graph showing fluorescence signal as a function of time due to $Ca^{2+}$ through a pore using no flow (thin solid line) or 100 µl/min flow (thick solid line) through the cis chamber. Dashed line represents a best-fit curve for the no-flow measurement. Experimental conditions are provided in the text.

Similar to other fluorescent reporter molecules, Fluo-8 is prone to photobleaching upon exposure to laser excitation. FIG. 4A shows the exponential decay of the fluorescence intensity over time with a time constant $\tau \approx 1.6$ s, available from the fit. This implies that the fluorescent signal drops 5% over 80 ms or 50% in 1.1 s due to photobleaching. A brief calculation suggests that at these time scales diffusion alone is unable to warrant a supply of fresh dye molecules and prevent signal loss. It is assumed that the diffusion constant (D) for the dye is that of fluorescein, D≈420 nm2/µs, 42 and that 2D diffusion away from the laser spot can be described by $<x^2> = 4Dt$, so the displacement x=20 µm in ~240 ms. The laser spot size used is of the order of 50 µm in diameter, which implies that with no flow a dye molecule is exposed to illumination for at least 600 ms. However, if buffer is pumped through the cis chamber at a rate of 100 µL/min, dye molecules remain illuminated for as short as 12.5 ms, given the distance between the glass and the chip, 0.2 mm, and the channel width of 2 mm. FIG. 4A demonstrates that such flow rate is sufficient to maintain the fluorescence intensity within 95% of its maximum for prolonged ion current measurements.

Figure 4C:
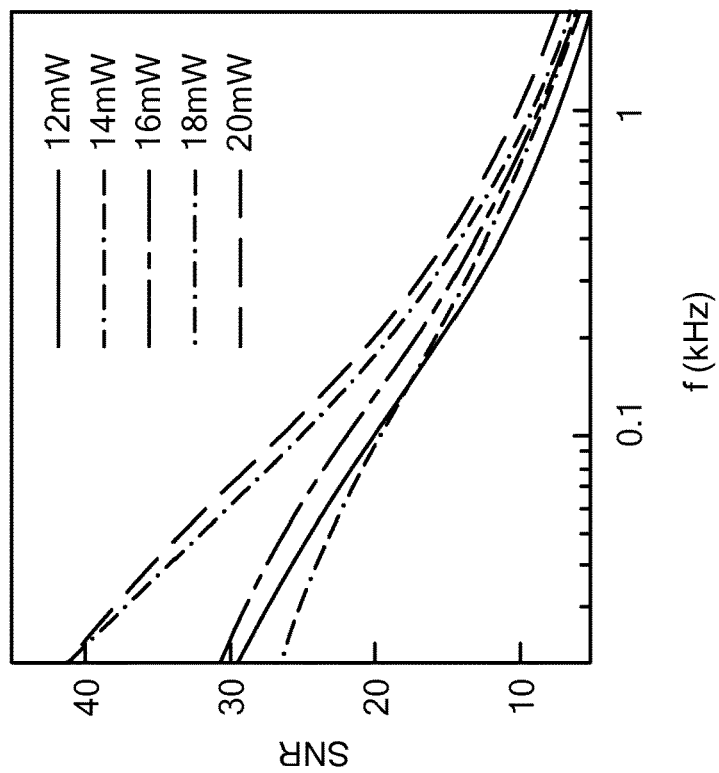
FIG. 4C is a graph showing the signal-to-noise ratio (SNR) as a function of bandwidth due to $Ca^{2+}$ through a pore using applied laser powers of 12 mW, 14 mW, 16 mW, 18 mW, and 20 mW or power intensities of 1-1000 mW/µm$^2$ (see figure legend for line identification of curves from different laser powers).
Figure 4B:
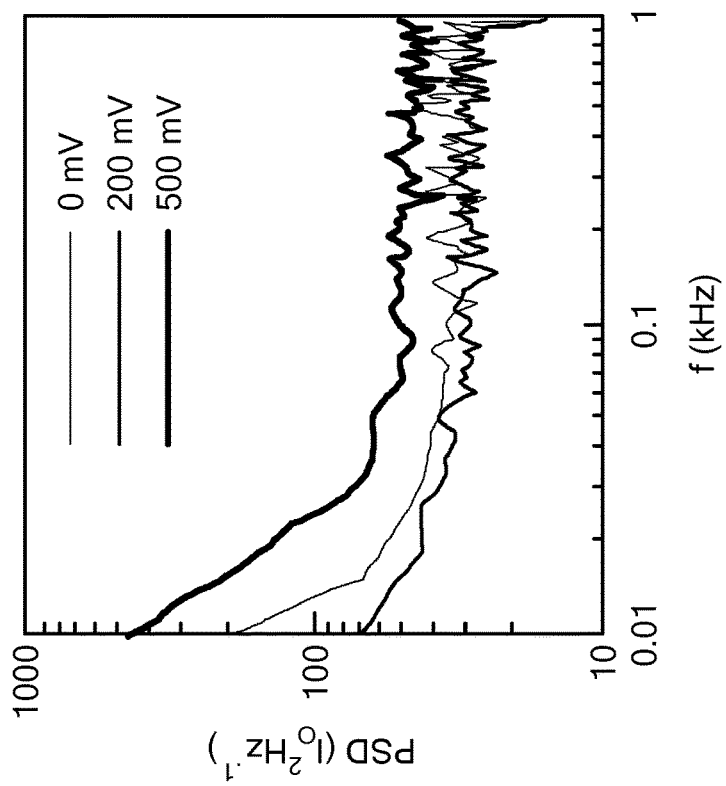
FIG. 4B is a graph showing the pore noise power spectral density (PSD) as a function of bandwidth due to $Ca^{2+}$ through a pore using no applied potential (thin line) and applied potentials of 200 mV (medium line) and 500 mV (thick line).

Nanopore noise power spectral density (PSD) for the optical signal readout at different voltages is presented in FIG. 4B. At frequencies below 100 Hz, all traces display 1/f-type noise, followed with a relatively flat region up to 1 kHz. Because optical sensing assesses the same phenomenon as patch-clamp measurements, namely, transport of ions through a pore, it is anticipated that nanopore noise for both readouts is of the same nature. The low 1/f flicker noise has been recently shown to arise from fluctuations in the number of charge carriers in a solid-state pore.[43] The Johnson noise arising from thermal fluctuations in the nanopore resistance dominates 1/f noise at higher frequencies (100 Hz to 1 kHz range). For 1 kHz sampling rate, the noise of the optical signal is negligibly affected by applying 200 mV bias; however, it increases 1.6 times when 500 mV is applied.

Although an increase in laser power can lead to the excitation of a larger volume of sample, and consequently higher optical signal, it may also result in higher noise, thus compromising the overall signal-to-noise ratio (SNR). SNR=$<I_O>/I_{noise,RMS}$, where $<I_O>$ is the mean of the optical signal and $I_{noise,RMS}=(\int_O^{BW} S_1 \, df)^{1/2}$ is the root-mean-square current noise, where BW is the bandwidth. SNR can be improved by raising the laser power, as shown in FIG. 4C; an increase in laser power from 12 to 20 mW leads to an improvement of SNR from 7.6 to 9.9. Furthermore, >7 independent measurements in various pores have showed a stable SNR value of 8.9±2.2 (1 kHz sampling rate, 400 mV bias, 20 mW laser power). It is anticipated that the use of high laser power densities can result in pore heating[44] and surface charge effects[45] that may negatively impact the SNR, although the data in FIG. 4C indicates that the conditions used here are well below this regime.

To assess the parallelization potential of optical readout as well as the correlation between electrical and optical signals, optical signal response to changing voltage, an analogue of I-V curves, was studied. Arrays of 800×800 nm-thinned regions were patterned onto the membrane sides of the chips, to assist in optical localization of nanopores. In addition, it has been previously shown that the thinning of membranes can increase signal amplitude for biomolecule detection.[46] FIG. 5A displays an SEM image of a typical nanopore array used in these experiments. Three nanopores with similar 3 nm diameters were drilled in the thinned regions indicated in the figure. The inset of FIG. 5A shows a transmission electron microscopy image of a typical 3 nm diameter pore.

Figures 5A, 5B:
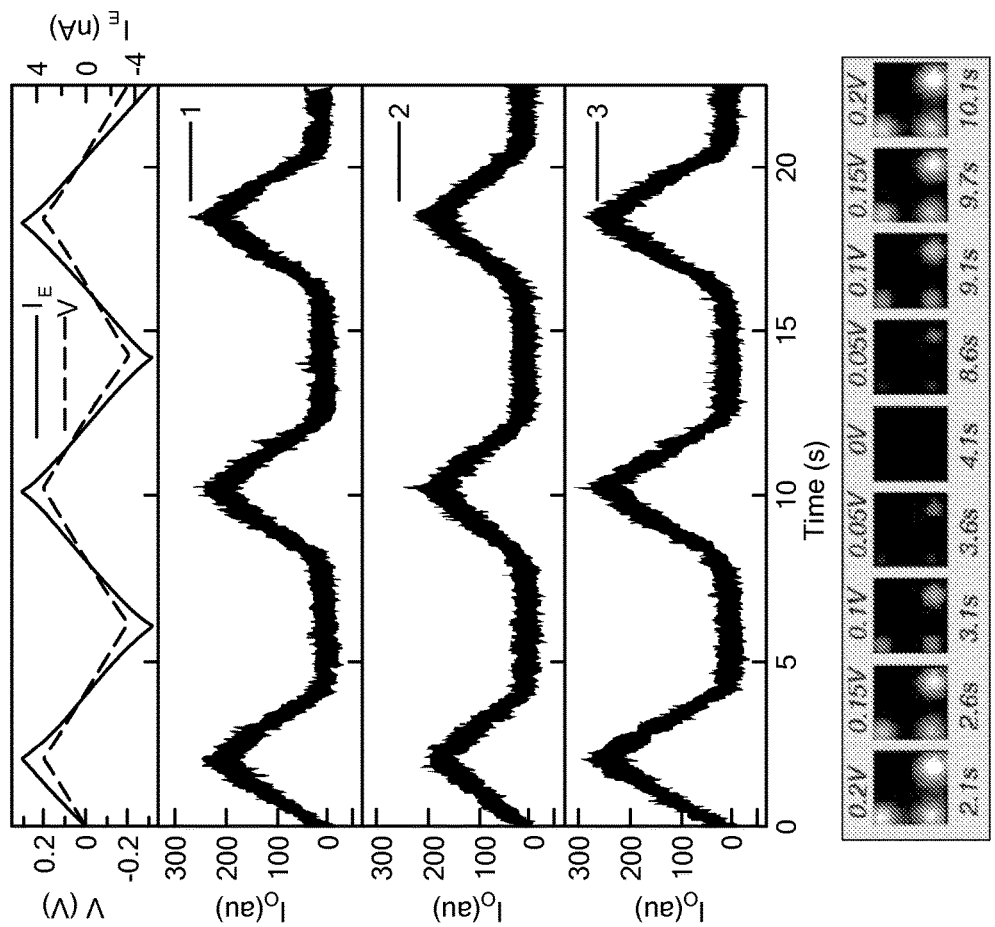
FIG. 5A is a scanning electron microscopy (SEM) image of a chip with four locally thinned regions and with a 3-nm pore drilled in of each the thinned regions except the one shown in the upper right. Pore 1 is in thinned region in upper left of image, pore 2 is in thinned region in lower left of image, and pore 3 is in thinned region in lower right of image. Inset is a transmission electron microscopy (TEM) image of a typical pore.
FIG. 5B shows the electrical and optical signals from $Ca^{2+}$ flux through a 3-pore chip with 65 mM of $CaCl_2$ in trans and 6.5 µM of Fluo-4 in cis chamber. Upper panel shows the applied potential (dashed line) and cumulative measured $I_E$ (solid line). Second panel from top shows $I_O$ of pore 1, third panel from top shows $I_O$ of pore 2, and fourth panel from top shows $I_O$ of pore 3. Bottom panel show images of fluorescence signal at indicated potentials (above each image) and time points (below each image).

FIG. 5B shows an example of simultaneous optical and electrical measurements of ionic flow through 3 nanopores as the voltage is repeatedly swept from −200 to +200 mV. The figure clearly shows that when a positive bias is applied a proportional increase in fluorescence can be observed at the location of any open pores, while a negative bias yields no increase in intensity as expected. The bottom panel of FIG. 5B shows that no crosstalk is observed for an array of 3 nm diameter nanopores with ~4 µm spacing, and it is important to note that the spacing can be further reduced as the nanopore diameter is reduced. In all experiments, the ionic current varies linearly with voltage, and similarly it can be seen that the fluorescent intensity from each pore varies linearly with voltage. Linear fits to the data yield the value of nanopore resistance. The resistance obtained from these measurements is 39.6 MΩ across all three pores.

To demonstrate the single molecule sensing ability of this system, a chip containing a single nanopore, 2.7 nm in diameter and 2 nm in effective thickness, was assembled as previously described, and a 1 nM concentration of 1000 bp dsDNA was added to the cis chamber buffer. Buffer was pumped through the cis chamber at a steady rate of 100 μL/min to minimize signal loss due to photobleaching. FIG. 6A shows the resulting optical and electrical traces, with fluorescent intensity on the left axis and the ionic current on the right axis. For these traces a +200 mV bias was applied, optical data was collected at 4.8 kHz and downsampled to 1 kHz, while electrical data was collected at 20 kHz and low pass filtered to 10 kHz.

Figure 6C:
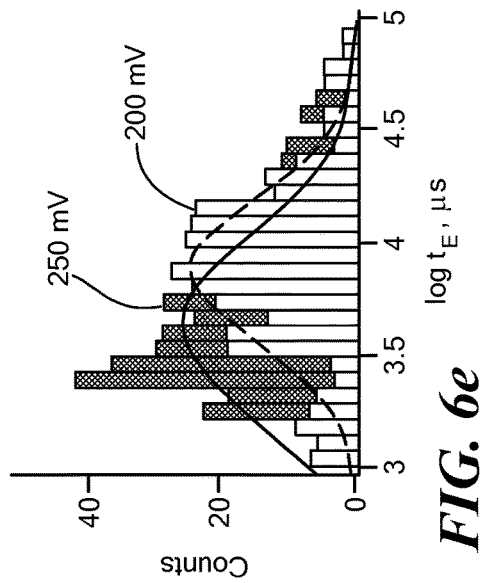
FIG. 6C is a $\Delta I_E/I_E^{Open}$ contour plot of a subset of the data from FIG. 6A encompassing 226 detected events. Population 1 represents translocation events, and population 2 represents DNA collisions.
Figure 6E:
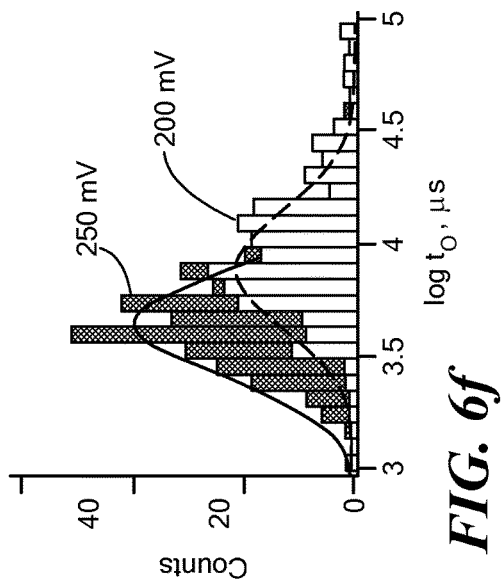
FIG. 6E is a histogram of electrically detected events at applied potentials of 250 mV (cross-hatched bars) and 200 mV (white bars). Solid line represents best-fit curve of 250 mV histogram, and dashed line represents best-fit curve of 200 mV histogram.
Figure 6D:
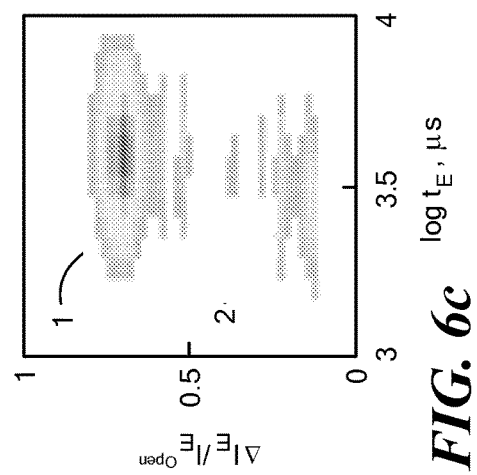
FIG. 6D is a $\Delta I_O/I_O^{Open}$ contour plot of the same subset of data shown in FIG. 6C. Note that only events in population 1, i.e., translocation events, are detectable optically.
Figure 6F:
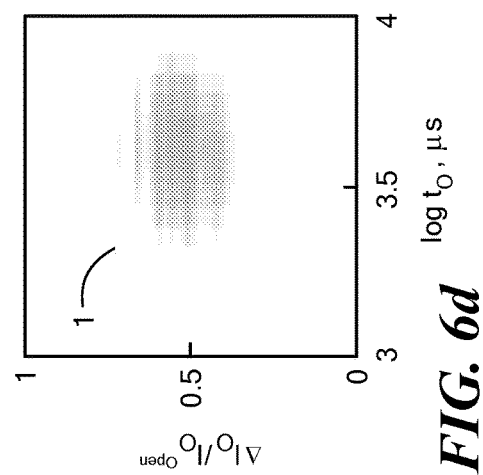
FIG. 6F is a histogram of optically detected events at applied potentials of 250 mV (cross-hatched bars) and 200 mV (white bars). Solid line represents best-fit curve of 250 mV histogram, and dashed line represents best-fit curve of 200 mV histogram.

The presence of a translocating analyte molecule within the pore causes characteristic transient drops in both optical intensity and ionic current. The changes in ionic current ($\Delta I$) and fluorescent intensity ($\Delta I_O$) are proportional to the number of ions the molecule excludes from the pore. The duration of the event, or dwell time ($t_d$), is defined by the amount of time the molecule resides in the pore. Both traces were analyzed and the dwell time measurements for each translocation event were extracted. Corresponding current drop values were extracted from electrical traces, and corresponding optical intensity drops were extracted from optical traces. Analysis was performed using the open source data analysis software OpenNanopore from the Radenovic lab at EPFL.[47] Examples of analyzed optical and electrical events are shown in FIG. 6B. FIG. 6C shows a contour plot for the translocation events detected electrically and FIG. 6D shows the corresponding data from optical measurements. A comparison of the two contour plots shows good agreement between dwell times for the translocation populations. FIG. 6E shows histograms for the log of the dwell time values observed in electrical measurements; data is presented for applied biases of 250 and 200 mV. Corresponding optical histograms are displayed in FIG. 6F. Gaussian fits to these histograms are displayed to estimate the peaks of the distributions. For 200 mV, electrical measurements indicate a most likely dwell time of 7.6 ms, while optical measurements suggest this value is 7.5 ms. For an applied voltage of 250 mV, the most likely dwell time observed electrically is 4.3 ms, whereas optically this value is 4.4 ms.

Figure 6G:
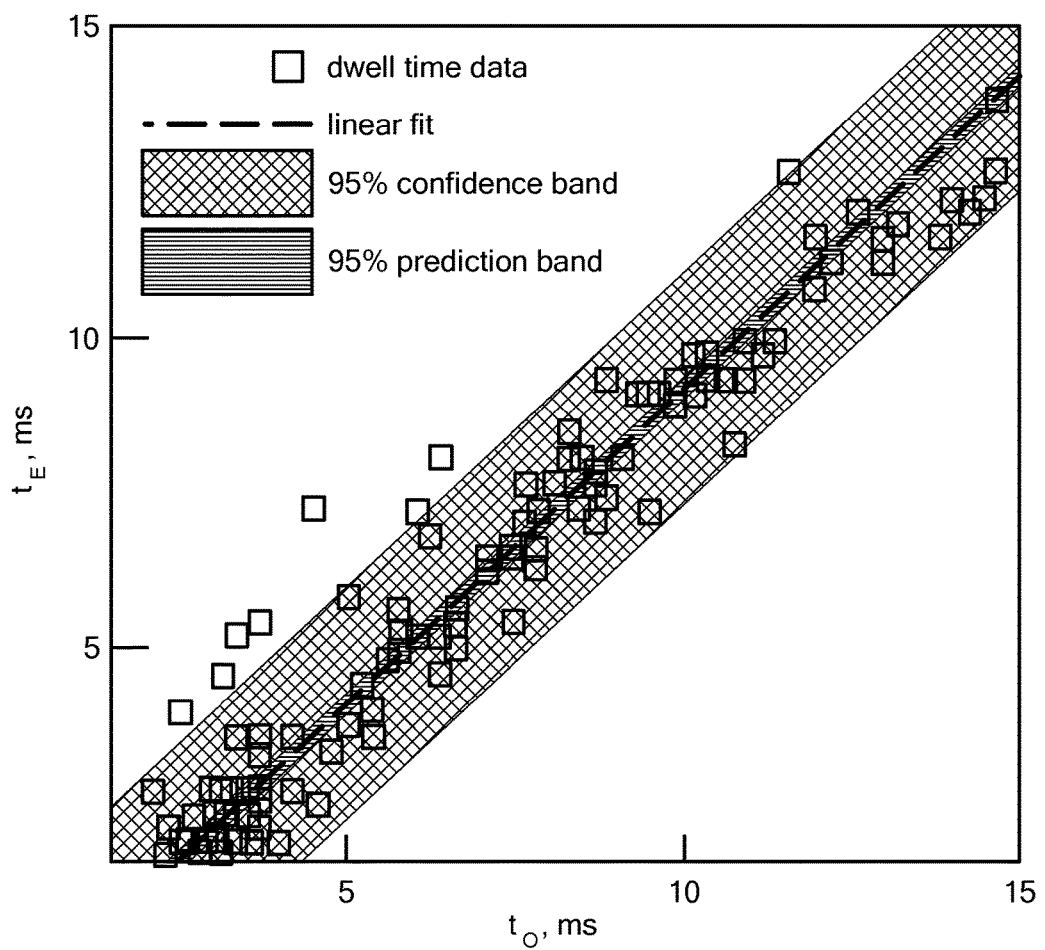
FIG. 6G is a graph showing the correlation between dwell times of dsDNA translocation detected electrically ($t_E$) and optically ($t_O$) in the range of 1.5-15 ms. Squares represent data points, dashed line represents best-fit line, cross-hatched area represents 95% confidence band, and pin-striped area represents 95% prediction band. Data were collected from 294 events collected over the course of 3 different experiments with 3 different pores that varied in size from 2.5 to 3.0 nm.

To further quantify the correlation between the two signals, observed electrical dwell time values were plotted against optical dwell time values for 294 events over 3 different single pore experiments (FIG. 6G). A perfect correlation between these two signals would result in the data forming a straight line with a slope of 1. A least-squares regression analysis of the data produced a line with a slope of 1.001±0.001. These results show a strong correlation between optical and electrical measurements, once again implying that optical measurements are able to access the same information as conventional nanopore experiments.

Electrical measurements suggest the presence of two distinctive populations of events (FIG. 6C). On the basis of the ionic current blockades $\Delta I_E/I_E^{Open}$ of 0.72±0.06 (1) and 0.18±0.09 (2) population 1 represents DNA translocation events, whereas population 2 presumably corresponds to collisions. Interestingly, the collision population 2 is completely missing in the optical scatter plot (FIG. 6D). Moreover, according to the optical measurements, DNA molecules block a smaller fraction of the ionic current with $\Delta I_O/I_O^{Open}$ comprising 0.56±0.15. Since the optical readout is selective to $Ca^{2+}$ ions, both of these discrepancies may be related to the difference in how $Ca^{2+}$ and monovalent ions interact with DNA.[48]

Notably, optical measurements maintain a high signal-to-noise ratio during DNA translocation; this ratio can be defined as $SNR_{DNA}=\Delta I_O/I_{noise,RMS}$, where $\Delta I_O$ is the drop in the optical intensity upon translocation of DNA. For 5 independent measurements, $SNR_{DNA}=7\pm1.5$ for a bias of 400 mV and 1 kHz sampling rate.

Figure 7A:
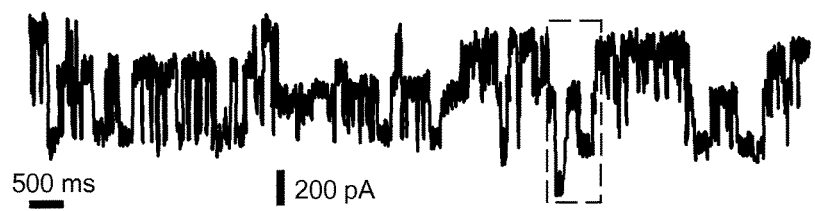
FIG. 7A is a cumulative electrical trace of translocation events of a 153 nt-long ssDNA through 3 sub-2 nm pores at the applied potential of 400 mV using 65 mM of $CaCl_2$ in trans and 6.5 µM of Fluo-8 in cis chamber.
Figure 7B:
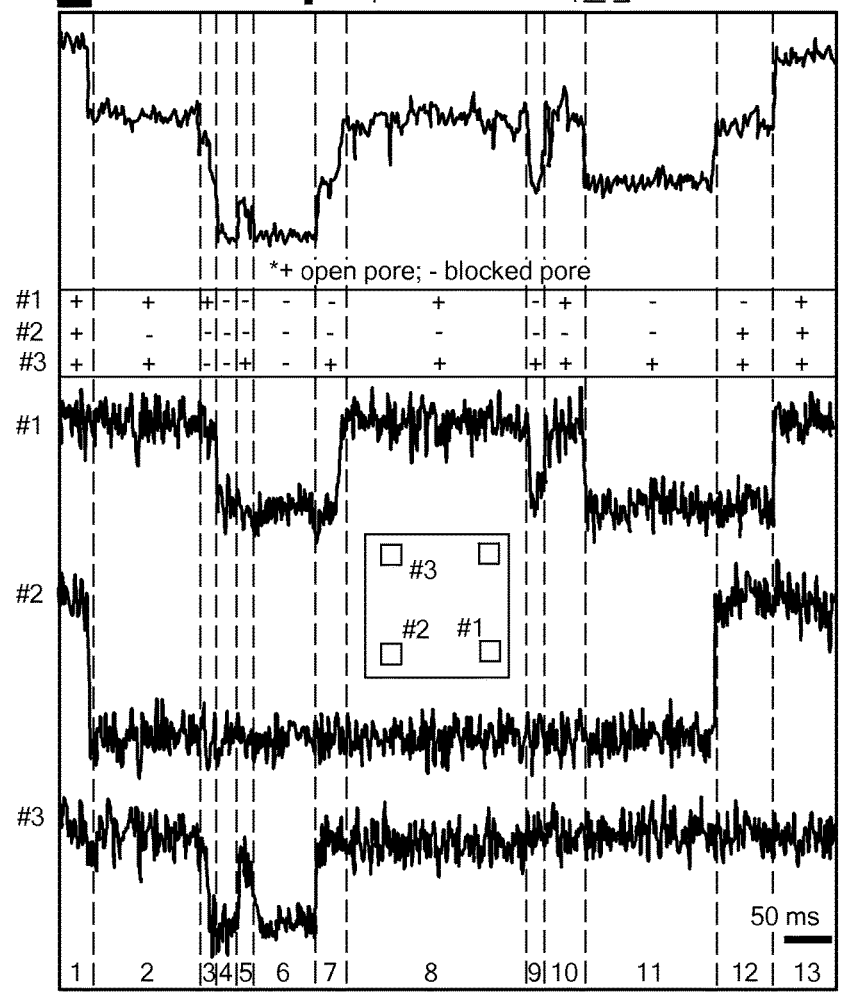
FIG. 7B shows the cumulative electrical trace (thin line at top) and individual optical traces (thick lines) from pores 1, 2, and 3 (as indicated) of the translocation events shown in the boxed region from FIG. 7A (note the difference in time scale between the traces in FIGS. 7A and 7B). Vertical dashed lines indicate boundaries of 13 arbitrary time frames (as indicated at bottom), and table between the electrical and optical traces indicates whether an individual pore was open (+) or blocked (−) during each time frame. Inset is a schematic of a portion of the chip showing four thinned regions and locations of pore 1 (lower right thinned region), pore 2 (lower left thinned region), and pore 3 (upper left thinned region).
Figure 7C:
FIG. 7C shows images of the averaged fluorescence intensity of the pores for each time frame as defined in FIG. 7B.

To display the scalability of this technique, an array of 3 sub-2 nm pores was drilled in a silicon nitride membrane and the system was assembled as before. For this experiment, 153 nt ssDNA was added to the previously described cis chamber buffer for a final concentration of 8 nM. A voltage bias of 400 mV was applied across the membrane, electrophoretically driving DNA molecules across all open pores. A representative electrical current trace can be seen in FIG. 7A. The multiple distinct levels that can be observed correspond to analyte molecules translocating through different combinations of the three open pores. However, electrical measurements only describe the collective behavior of the system and are unable to provide the information about individual pores. In contrast, optical readout of the ionic current allows us to trace every change in the electrical current to a specific pore (FIG. 7B). FIG. 7C shows the optical signals from the pores over the course of 13 changes in the electrical current trace.

REFERENCES

1. Branton, D.; Deamer, D. W.; Marziali, A.; Bayley, H.; Benner, S. A.; Butler, T.; Di Ventra, M.; Garaj, S.; Hibbs, A.; Huang, X.; et al. The Potential and Challenges of Nanopore Sequencing. Nat. Biotechnol. 2008, 26, 1146-1153.
2. Clarke, J.; Wu, H.-C.; Jayasinghe, L.; Patel, A.; Reid, S.; Bayley, H. Continuous Base Identification for Single-Molecule Nanopore DNA Sequencing. Nat. Nanotechnol. 2009, 4, 265-270.
3. Ayub, M.; Hardwick, S. W.; Luisi, B. F.; Bayley, H. Nanopore-Based Identification of Individual Nucleotides for Direct RNA Sequencing. Nano Lett. 2013, 13, 6144-6150.
4. Nivala, J.; Marks, D. B.; Akeson, M. Unfoldase-Mediated Protein Translocation through an Alpha-Hemolysin Nanopore. Nat. Biotechnol. 2013, 31, 247-250.
5. Rodriguez-Larrea, D.; Bayley, H. Multistep Protein Unfolding During Nanopore Translocation. Nat. Nanotechnol. 2013, 8, 288-295.
6. Rosen, C. B.; Rodriguez-Larrea, D.; Bayley, H. Single-Molecule Site-Specific Detection of Protein Phosphorylation with a Nanopore. Nat. Biotechnol. 2014, 32, 179-181.
7. Shasha, C.; Henley, R. Y.; Stoloff, D. H.; Rynearson, K. D.; Hermann, T.; Wanunu, M. Nanopore-Based Conformational Analysis of a Viral RNA Drug Target. ACS Nano 2014, 8, 6425-6430.
8. Arnaut, V.; Langecker, M.; Simmel, F. C. Nanopore Force Spectroscopy of Aptamer-Ligand Complexes. Biophys. J. 2013, 105, 1199-1207.
9. Keyser, U. F.; Koeleman, B. N.; Van Dorp, S.; Krapf, D.; Smeets, R. M. M.; Lemay, S. G.; Dekker, N. H.; Dekker, C. Direct Force Measurements on DNA in a Solid-State Nanopore. Nat. Phys. 2006, 2, 473-477.

10. Freedman, K. J.; Bastian, A. R.; Chaiken, I.; Kim, M. J. Solid-State Nanopore Detection of Protein Complexes: Applications in Healthcare and Protein Kinetics. Small 2013, 9, 750-759.
11. Japrung, D.; Dogan, J.; Freedman, K.; Nadzeyka, A.; Bauerdick, S.; Albrecht, T.; Kim, M. J.; Jemth, P.; Edel, J. B. Single-Molecule Studies of Intrinsically Disordered Proteins Using Solid-State Nanopores. Anal. Chem. 2013, 85, 2449-2456.
12. Larkin, J.; Henley, R. Y.; Muthukumar, M.; Rosenstein, J. K.; Wanunu, M. High-Bandwidth Protein Analysis Using Solid-State Nanopores. Biophys. J. 2014, 106, 696-704.
13. Li, W.; Bell, N. A. W.; Hernandez-Ainsa, S.; Thacker, V. V.; Thackray, A. M.; Bujdoso, R.; Keyser, U. F. Single Protein Molecule Detection by Glass Nanopores. ACS Nano 2013, 7, 4129-4134.
14. Chansin, G. A. T.; Mulero, R.; Hong, J.; Kim, M. J.; Demello, A. J.; Edel, J. B. Single-Molecule Spectroscopy Using Nanoporous Membranes. Nano Lett. 2007, 7, 2901-2906.
15. Soni, G. V.; Singer, A.; Yu, Z. L.; Sun, Y. J.; McNally, B.; Meller, A. Synchronous Optical and Electrical Detection of Biomolecules Traversing through Solid-State Nanopores. Rev. Sci. Instrum. 2010, 81, 014301.
16. McNally, B.; Singer, A.; Yu, Z. L.; Sun, Y. J.; Weng, Z. P.; Meller, A. Optical Recognition of Converted DNA Nucleotides for Single-Molecule DNA Sequencing Using Nanopore Arrays. Nano Lett. 2010, 10, 2237-2244.
17. Ando, G.; Hyun, C.; Li, J. L.; Mitsui, T. Directly Observing the Motion of DNA Molecules near Solid-State Nanopores. ACS Nano 2012, 6, 10090-10097.
18. Kurz, V.; Nelson, E. M.; Shim, J.; Timp, G. Direct Visualization of Single-Molecule Translocations through Synthetic Nanopores Comparable in Size to a Molecule. ACS Nano 2013, 7, 4057-4069.
19. Auger, T.; Mathe, J.; Viasnoff, V.; Charron, G.; Di Meglio, J. M.; Auvray, L.; Montel, F. Zero-Mode Waveguide Detection of Flow-Driven DNA Translocation through Nanopores. Phys. Rev. Lett. 2014, 113, 028302.
20. Ivanov, A. P.; Instuli, E.; McGilvery, C. M.; Baldwin, G.; McComb, D. W.; Albrecht, T.; Edel, J. B. DNA Tunneling Detector Embedded in a Nanopore. Nano Lett. 2011, 11, 279-285.
21. Tsutsui, M.; Matsubara, K.; Ohshiro, T.; Furuhashi, M.; Taniguchi, M.; Kawai, T. Electrical Detection of Single Methylcytosines in a DNA Oligomer. J. Am. Chem. Soc. 2011, 133, 9124-9128.
22. Healy, K.; Ray, V.; Willis, L. J.; Peterman, N.; Bartel, J.; Drndic, M. Fabrication and Characterization of Nanopores with Insulated Transverse Nanoelectrodes for DNA Sensing in Salt Solution. Electrophoresis 2012, 33, 3488-3496.
23. Xie, P.; Xiong, Q. H.; Fang, Y.; Qing, Q.; Lieber, C. M. Local Electrical Potential Detection of DNA by Nanowire-Nanopore Sensors. Nat. Nano 2012, 7, 119-125.
24. Krishnakumar, P.; Gyarfas, B.; Song, W. S.; Sen, S.; Zhang, P. M.; Krstic, P.; Lindsay, S. Slowing DNA Trans Location through a Nanopore Using a Functionalized Electrode. ACS Nano 2013, 7, 10319-10326.
25. Traversi, F.; Raillon, C.; Benameur, S. M.; Liu, K.; Khlybov, S.; Tosun, M.; Krasnozhon, D.; Kis, A.; Radenovic, A. Detecting the Translocation of DNA through a Nanopore Using Graphene Nanoribbons. Nat. Nano 2013, 8, 939-945.
26. Zhao, Y. A.; Ashcroft, B.; Zhang, P. M.; Liu, H.; Sen, S. M.; Song, W.; Im, J.; Gyarfas, B.; Manna, S.; Biswas, S.; et al. Single-Molecule Spectroscopy of Amino Acids and Peptides by Recognition Tunnelling. Nat. Nanotechnol. 2014, 9, 466-473.
27. Baaken, G.; Ankri, N.; Schuler, A.-K.; Ruehe, J.; Behrends, J. C. Nanopore-Based Single-Molecule Mass Spectrometry on a Lipid Membrane Microarray. ACS Nano 2011, 5, 8080-8088.
28. Bell, N. A. W.; Thacker, V. V.; Hernandez-Ainsa, S.; Fuentes-Perez, M. E.; Moreno-Herrero, F.; Liedl, T.; Keyser, U. F. Multiplexed Ionic Current Sensing with Glass Nanopores. Lab Chip 2013, 13, 1859-1862.
29. Osaki, T.; Suzuki, H.; Le Pioufle, B.; Takeuchi, S. Multichannel Simultaneous Measurements of Single-Molecule Translocation in Alpha-Hemolysin Nanopore Array. Anal. Chem. 2009, 81, 9866-9870.
30. Maitra, R. D.; Kim, J.; Dunbar, W. B. Recent Advances in Nanopore Sequencing. Electrophoresis 2012, 33, 3418-3428.
31. Rothberg, J. M.; Hinz, W.; Rearick, T. M.; Schultz, J.; Mileski, W.; Davey, M.; Leamon, J. H.; Johnson, K.; Milgrew, M. J.; Edwards, M.; et al. An Integrated Semiconductor Device Enabling Non-Optical Genome Sequencing. Nature 2011, 475, 348-352.
32. Demuro, A.; Parker, I. Optical Single-Channel Recording: Imaging $Ca^{2+}$ Flux through Individual N-Type Voltage-Gated Channels Expressed in Xenopus Oocytes. Cell Calcium 2003, 34, 499-509.
33. Demuro, A.; Parker, I. Imaging the Activity and Localization of Single Voltage-Gated $Ca^{2+}$ Channels by Total Internal Reflection Fluorescence Microscopy. Biophys. J. 2004, 86, 3250-3259.
34. Demuro, A.; Parker, I. "Optical Patch-Clamping": Single-Channel Recording by Imaging $Ca^{2+}$ Flux through Individual Muscle Acetylcholine Receptor Channels. J. Gen Phys. 2005, 126, 179-192.
35. Shuai, J. W.; Parker, I. Optical Single-Channel Recording by Imaging $Ca^{2+}$ Flux through Individual Ion Channels: Theoretical Considerations and Limits to Resolution. Cell Calcium 2005, 37, 283-299.
36. Manrao, E. A.; Derrington, I. M.; Laszlo, A. H.; Langford, K. W.; Hopper, M. K.; Gillgren, N.; Pavlenok, M.; Niederweis, M.; Gundlach, J. H. Reading DNA at Single-Nucleotide Resolution with a Mutant Mspa Nanopore and Phi29 DNA Polymerase. Nat. Biotechnol. 2012, 30, 349-353.
37. Laszlo, A. H.; Derrington, I. M.; Brinkerhoff, H.; Langford, K. W.; Nova, I. C.; Samson, J. M.; Bartlett, J. J.; Pavlenok, M.; Gundlach, J. H. Detection and Mapping of 5-Methylcytosine and 5-Hydroxymethylcytosine with Nanopore Mspa. Proc. Natl. Acad. Sci. U.S.A. 2013, 110, 18904-18909.
38. Schreiber, J.; Wescoe, Z. L.; Abu-Shumays, R.; Vivian, J. T.; Baatar, B.; Karplus, K.; Akeson, M. Error Rates for Nanopore Discrimination among Cytosine, Methylcytosine, and Hydroxymethylcytosine Along Individual DNA Strands. Proc. Natl. Acad. Sci. U.S.A. 2013, 110, 18910-18915.
39. Cherf, G. M.; Lieberman, K. R.; Rashid, H.; Lam, C. E.; Karplus, K.; Akeson, M. Automated Forward and Reverse Ratcheting of DNA in a Nanopore at 5-Angstrom Precision. Nat. Biotechnol. 2012, 30, 344-348.
40. Sonnleitner, A.; Isacoff, E. Single Ion Channel Imaging. Methods Enzymol. 2003, 361, 304-319.
41. Heron, A. J.; Thompson, J. R.; Cronin, B.; Bayley, H.; Wallace, M. I. Simultaneous Measurement of Ionic Current and Fluorescence from Single Protein Pores. J. Am. Chem. Soc. 2009, 131, 1652-1653.
42. Lukacs, G. L.; Haggie, P.; Seksek, O.; Lechardeur, D.; Freedman, N.; Verkman, A. S. Size-Dependent DNA Mobility in Cytoplasm and Nucleus. J. Biol. Chem. 2000, 275, 1625-1629.
43. Smeets, R. M. M.; Keyser, U. F.; Dekker, N. H.; Dekker, Noise in Solid-State Nanopores. Proc. Natl. Acad. Sci. U.2008, 105, 417-421.
44. Keyser, U. F.; Krapf, D.; Koeleman, B. N.; Smeets, R. M. Dekker, N. H.; Dekker, C. Nanopore Tomography of a Laser Focus. Nano Lett. 2005, 5, 2253-2256.
45. Di Fiori, N.; Squires, A.; Bar, D.; Gilboa, T.; Moustakas, T. Meller, A. Optoelectronic Control of Surface Charge Translocation Dynamics in Solid-State Nanopores. Nat. Nano 2013, 8, 946-951.
46. Wanunu, M.; Dadosh, T.; Ray, V.; Jin, J.; McReynolds, Drndic, M. Rapid Electronic Detection of Probe-Specific Micrornas Using Thin Nanopore Sensors. Nat. Nanotechnol. 2010, 5, 807-814.
47. Raillon, C.; Granjon, P.; Graf, M.; Steinbock, L. J.; Radenovic, A. Fast and Automatic Processing of Multi-Level Events Nanopore Translocation Experiments. Nanoscale 2012, 4916-4924.
48. Egli, M. DNA-Cation Interactions: Quo Vadis? Chem. Biol. 2002, 9, 277-286.
49. Kim, M. J.; Wanunu, M.; Bell, D. C.; Meller, A. Rapid Fabrication of Uniformly Sized Nanopores and Nanopore Arrays for Parallel DNA Analysis. Adv. Mater. 2006, 18, 3149-3155.
50. Sawafta, F.; Clancy, B.; Carlsen, A. T.; Huber, M.; Hall, A. Solid-State Nanopores and Nanopore Arrays Optimized for Optical Detection. Nanoscale 2014, 6, 6991-6996.
51. Wanunu, M.; Meller, A. Chemically Modified Solid-State Nanopores. Nano Lett. 2007, 7, 1580-1585.

What is claimed is:

1. A method of determining a sequence of a polynucleotide, the method comprising the steps of:
   (a) providing a system comprising
      (1) a first reservoir comprising a first electrically conductive aqueous solution comprising a fluorescent reporter molecule capable of producing a fluorescence emission that is altered in the presence of an ionic species;
      (2) a first electrode disposed in the first reservoir in electrical contact with the first electrically conductive aqueous solution;
      (3) a second reservoir comprising a second electrically conductive aqueous solution comprising the ionic species;
      (4) a second electrode disposed in the second reservoir and in electrical contact with the second electrically conductive aqueous solution; and
      (5) a membrane separating the first reservoir and second reservoir, the membrane having a pore through which members of the ionic species can pass;
      wherein the first electrically conductive aqueous solution in the first reservoir further comprises the polynucleotide or a complex containing the polynucleotide;
      wherein the membrane further comprises a single polynucleotide polymerase immobilized on the membrane within 100 nm of the pore, and the polynucleotide polymerase is in contact with the first electrically conductive aqueous solution;
      wherein the first electrically conductive aqueous solution in the first reservoir further comprises at least four deoxyribonucleotide polyphosphate (dNPP) analogs, wherein incorporation of each dNPP analog during DNA strand synthesis by the polynucleotide polymerase results in release of a different polyphosphate-tag moiety;
      wherein the polynucleotide is a primed single-stranded template;
   (b) allowing the polynucleotide polymerase to form a complex with the primed single-stranded template;
   (c) allowing the polynucleotide polymerase to mediate nucleic acid synthesis using the at least four deoxyribonucleotide polyphosphate (dNPP) analogs;
   (d) applying a light signal capable of exciting the fluorescent reporter molecule to a region in the first reservoir proximal to the pore;
   (e) applying an electric field between the first and second electrodes, the electric field causing:
      (i) members of the ionic species to pass through the pore from the second reservoir to the first reservoir and bind to the fluorescent reporter molecule, thereby producing a change in the fluorescence emission from the fluorescent reporter molecule; and
      (ii) the polyphosphate-tag moieties to pass through the pore from the first reservoir to the second reservoir, whereby transit of members of the ionic species through the pore is reduced and the change in the fluorescence emission from the fluorescent reporter molecule is attenuated differently by each polyphosphate-tag moiety; and
   (f) measuring the fluorescence signal so as to determine the nucleotide sequence of the polynucleotide.

2. A method of determining a sequence of a polynucleotide, the method comprising the steps of:
   (a) providing a system comprising
      (1) a first reservoir comprising a first electrically conductive aqueous solution comprising a fluorescent reporter molecule capable of producing a fluorescence emission that is altered in the presence of an ionic species;
      (2) a first electrode disposed in the first reservoir in electrical contact with the first electrically conductive aqueous solution;
      (3) a second reservoir comprising a second electrically conductive aqueous solution comprising the ionic species;
      (4) a second electrode disposed in the second reservoir and in electrical contact with the second electrically conductive aqueous solution; and
      (5) a membrane separating the first reservoir and second reservoir, the membrane having a pore through which members of the ionic species can pass;
      wherein the first electrically conductive aqueous solution in the first reservoir further comprises the polynucleotide or a complex containing the polynucleotide;
      wherein the first electrically conductive aqueous solution in the first reservoir further comprises a polynucleotide polymerase;
      wherein the polynucleotide is a primed single-stranded template;
   (b) allowing the polynucleotide polymerase to form a complex with the primed single-stranded template;
   (c) applying a light signal capable of exciting the fluorescent reporter molecule to a region in the first reservoir proximal to the pore;

(d) applying an electric field between the first and second electrodes, the electric field causing:
  (i) members of the ionic species to pass through the pore from the second reservoir to the first reservoir and bind to the fluorescent reporter molecule, thereby producing a change in the fluorescence emission from the fluorescent reporter molecule; and
  (ii) the single-stranded portion of the template to pass through the pore from the first reservoir to the second reservoir, thereby causing the complex to be retained in the pore;
(e) allowing the polynucleotide polymerase to mediate nucleic acid synthesis, thereby pulling the single-stranded portion of the template through the pore from the second reservoir to the first reservoir, whereby transit of members of the ionic species through the pore is reduced and the change in the fluorescence emission from the fluorescent reporter molecule is attenuated differently for each type of nucleotide in the polynucleotide; and
(f) measuring the fluorescence signal so as to determine the nucleotide sequence of the polynucleotide.

3. A method of determining a sequence of a polynucleotide, the method comprising the steps of:
(a) providing a system comprising
  (1) a first reservoir comprising a first electrically conductive aqueous solution comprising a fluorescent reporter molecule capable of producing a fluorescence emission that is altered in the presence of an ionic species;
  (2) a first electrode disposed in the first reservoir in electrical contact with the first electrically conductive aqueous solution;
  (3) a second reservoir comprising a second electrically conductive aqueous solution comprising the ionic species;
  (4) a second electrode disposed in the second reservoir and in electrical contact with the second electrically conductive aqueous solution; and
  (5) a membrane separating the first reservoir and second reservoir, the membrane having a pore through which members of the ionic species can pass;
  wherein the first electrically conductive aqueous solution in the first reservoir further comprises the polynucleotide or a complex containing the polynucleotide;
  wherein the first electrically conductive aqueous solution in the first reservoir further comprises a helicase;
  wherein the polynucleotide has a single-stranded portion and a double-stranded portion:
(b) allowing the helicase to form a complex with the polynucleotide;
(c) applying a light signal capable of exciting the fluorescent reporter molecule to a region in the first reservoir proximal to the pore;
(d) applying an electric field between the first and second electrodes, the electric field causing:
  (i) members of the ionic species to pass through the pore from the second reservoir to the first reservoir and bind to the fluorescent reporter molecule, thereby producing a change in the fluorescence emission from the fluorescent reporter molecule; and
  (ii) the single-stranded portion of the polynucleotide to pass through the pore from the first reservoir to the second reservoir, thereby causing the complex to be retained in the pore;
(e) allowing the helicase to separate the strands of the double-stranded portion of the polynucleotide, thereby allowing the single-stranded portion to continue to pass through the pore, whereby transit of members of the ionic species through the pore is reduced and the change in the fluorescence emission from the fluorescent reporter molecule is attenuated differently for each type of nucleotide in the polynucleotide; and
(f) measuring the fluorescence signal so as to determine the nucleotide sequence of the polynucleotide.

4. A system for analyzing a polynucleotide or a complex comprising the polynucleotide, the system comprising:
(a) a first reservoir comprising a first electrically conductive aqueous solution comprising a fluorescent reporter molecule capable of producing a fluorescence emission that is altered in the presence of an ionic species; and
(b) a first electrode disposed in the first reservoir in electrical contact with the first electrically conductive aqueous solution;
(c) a second reservoir comprising a second electrically conductive aqueous solution comprising the ionic species;
(d) a second electrode disposed in the second reservoir and in electrical contact with the second electrically conductive aqueous solution; and
(e) a membrane separating the first reservoir and second reservoir, the membrane having a pore through which members of the ionic species can pass; wherein
  (i) the membrane further comprises a single polynucleotide polymerase immobilized on the membrane within 100 nm of the pore, and the polynucleotide polymerase is in contact with the first electrically conductive aqueous solution, or
  (ii) the first electrically conductive aqueous solution in the first reservoir comprises a polynucleotide polymerase and the polynucleotide is a primed single-stranded template, or
  (iii) the first electrically conductive aqueous solution in the first reservoir comprises a helicase and the polynucleotide has a single-stranded portion and a double-stranded portion,
wherein the system is configured to sequence the polynucleotide based on different said fluorescence emissions.

5. The system of claim 4, wherein the pore has a diameter from about 0.3 to about 5 nm.

6. The system of claim 4, wherein the pore has a longitudinal length from about 0.3 nm to about 2.5 nm.

7. The system of claim 4, wherein the membrane comprises a material selected from the group consisting of silicon, silicon nitride, silicon dioxide, mica, hafnium oxide, molybdenum disulfide, and polyimide.

8. The system of claim 4, wherein the first reservoir further comprises the polynucleotide or complex containing the polynucleotide.

9. The system of claim 8, wherein the first electrically conductive aqueous solution in the first reservoir further comprises the polynucleotide polymerase of (e)(ii).

10. The system of claim 8, wherein the first electrically conductive aqueous solution in the first reservoir further comprises the helicase of (e)(iii).

11. The system of claim 8, wherein the membrane further comprises a single polynucleotide polymerase immobilized on the membrane within 100 nm of the pore, and the polynucleotide polymerase is in contact with the first electrically conductive aqueous solution.

12. The system of claim 11, wherein the first electrically conductive aqueous solution in the first reservoir further comprises at least four deoxyribonucleotide polyphosphate (dNPP) analogs, wherein incorporation of each dNPP analog during DNA strand synthesis by the polynucleotide polymerase results in release of a different polyphosphate-tag moiety.

13. The system of claim 4, wherein transit of a portion of the polynucleotide through the pore impedes passage of members of the ionic species through the pore.

14. The system of claim 12, wherein the membrane comprises at least 100 pores.

* * * * *

UNITED STATES PATENT AND TRADEMARK OFFICE
CERTIFICATE OF CORRECTION

PATENT NO. : 10,047,392 B2
APPLICATION NO. : 15/119859
DATED : August 14, 2018
INVENTOR(S) : Andrey Ivankin et al.

Page 1 of 1

It is certified that error appears in the above-identified patent and that said Letters Patent is hereby corrected as shown below:

In the Specification

Column 1, Line 16, delete:
"This invention was developed with financial support from Grant Nos. R21-HG006873 and R01-HG006321 from the National Institutes of Health and from Grant No. ECCS-00335765 from the National Science Foundation. The U.S. Government has certain rights in the invention."

And insert the following:
--This invention was made with government support under Grant Numbers HG006873 and HG006321 awarded by the National Institutes of Health, and Grant Number ECCS-0335767 awarded by the National Science Foundation. The government has certain rights in the invention.--

Signed and Sealed this
First Day of December, 2020

Andrei Iancu
*Director of the United States Patent and Trademark Office*